United States Patent
Leeper et al.

(10) Patent No.: US 11,253,588 B2
(45) Date of Patent: *Feb. 22, 2022

(54) COMBINATION THERAPY FOR TREATMENT OF CORONARY ARTERY DISEASE

(71) Applicant: The Board of Trustees of the Leland Stanford Junior University, Stanford, CA (US)

(72) Inventors: Nicholas J. Leeper, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 921 days.

This patent is subject to a terminal disclaimer.

(21) Appl. No.: 15/551,881

(22) PCT Filed: Feb. 25, 2016

(86) PCT No.: PCT/US2016/019633
§ 371 (c)(1),
(2) Date: Aug. 17, 2017

(87) PCT Pub. No.: WO2016/138306
PCT Pub. Date: Sep. 1, 2016

(65) Prior Publication Data
US 2018/0028651 A1 Feb. 1, 2018

Related U.S. Application Data

(60) Provisional application No. 62/126,260, filed on Feb. 27, 2015.

(51) Int. Cl.
| | | |
|---|---|---|
| A61K 39/395 | (2006.01) | |
| C07K 16/24 | (2006.01) | |
| C07K 16/28 | (2006.01) | |
| A61K 38/17 | (2006.01) | |
| A61K 45/06 | (2006.01) | |
| A61P 9/10 | (2006.01) | |
| A61K 39/00 | (2006.01) | |

(52) U.S. Cl.
CPC .......... *A61K 39/3955* (2013.01); *A61K 38/17* (2013.01); *A61K 38/1709* (2013.01); *A61K 38/179* (2013.01); *A61K 38/1793* (2013.01); *A61K 39/39541* (2013.01); *A61K 45/06* (2013.01); *A61P 9/10* (2018.01); *C07K 16/241* (2013.01); *C07K 16/2803* (2013.01); *A61K 2039/505* (2013.01); *A61K 2039/507* (2013.01); *C07K 2317/24* (2013.01); *C07K 2317/732* (2013.01); *C07K 2317/76* (2013.01); *C07K 2319/30* (2013.01)

(58) Field of Classification Search
CPC .......... A61K 2039/505; A61K 39/3955; A61K 39/39558; A61K 39/001111; A61K 39/001138; C07K 16/241; C07K 16/28; C07K 16/2803; C07K 16/2839; C07K 2317/76; C07K 2317/24; C07K 2319/30
See application file for complete search history.

(56) References Cited

U.S. PATENT DOCUMENTS

| | | | | |
|---|---|---|---|---|
| 5,919,452 | A | * 7/1999 | Le | C07K 14/525 424/133.1 |
| 10,329,354 | B2 | * 6/2019 | Leeper | A61K 38/177 |
| 2001/0021380 | A1 | 9/2001 | Pluenneke | |
| 2010/0092467 | A1 | 4/2010 | Isenberg | |
| 2012/0039896 | A1 | 2/2012 | Clemmons et al. | |
| 2012/0269731 | A1 | * 10/2012 | Wellstein | C07K 14/4737 424/9.1 |
| 2014/0161799 | A1 | 6/2014 | Frazier et al. | |

FOREIGN PATENT DOCUMENTS

| | | |
|---|---|---|
| WO | 2001/043743 A1 | 6/2001 |
| WO | WO2001/43743 | 6/2001 |
| WO | 2010070047 A1 | 6/2010 |
| WO | WO2010/070047 | 6/2010 |
| WO | 2011/143624 A2 | 11/2011 |
| WO | 2012170250 A1 | 12/2012 |
| WO | WO2012/170250 | 12/2012 |
| WO | 2013/032883 A2 | 3/2013 |
| WO | WO2013/032883 | 3/2013 |
| WO | 2014/124028 A1 | 8/2014 |
| WO | WO2014/124028 | 8/2014 |
| WO | 2014/149477 A1 | 9/2014 |
| WO | WO2014/149477 | 9/2014 |
| WO | 2015/041987 A1 | 3/2015 |

(Continued)

OTHER PUBLICATIONS

Ring, N.G., et al. Anti-SIRPalpha antibody immunotherapy enhances neutrophil and macrophage antitumor activity. Proc. Natl. Acad. Sci., 2017, 114(49):E10578-E10585.*
Soto-Pantoja, D.R. et al. Therapeutic opportunities for targeting the ubiquitous cell surface receptor CD47. Expert. Opin. Ther. Targets, 2013, 17(1):89-103.*
Thomas, S.S. et al. Comparative immunogenicity of TNF inhibitors: Impact on clinical efficacy and tolerability in the management of autoimmune diseases. A systematic review and meta-analysis. BioDrugs, 2015, 29:241-258.*
Weiskoph, K., et al. Engineered SIRPalpha variants as immunotherapeutic adjuvants to anti-cancer antibodies. Science, 2013, 341 (6141), p. 1-13.*

(Continued)

*Primary Examiner* — Prema M Mertz
(74) *Attorney, Agent, or Firm* — Pamela J. Sherwood; Bozicevic, Field & Francis LLP

(57) ABSTRACT

An effective combined dose of an anti-CD47 agent and an anti-TNF agent is administered to the subject in a dose and for a period of time effective to stabilize, prevent or reduce atherosclerotic plaque in the individual.

6 Claims, 14 Drawing Sheets
(14 of 14 Drawing Sheet(s) Filed in Color)
Specification includes a Sequence Listing.

(56) References Cited

FOREIGN PATENT DOCUMENTS

| WO | WO2015/041987 | 3/2015 |
| WO | 2016/044021 A1 | 3/2016 |
| WO | WO2016/044021 | 3/2016 |

OTHER PUBLICATIONS

Oberoi, R., et al. Anti-tumor necrosis factor-alpha therapy increases plaque burden in a mouse model of experimental atherosclerosis. Atherosclerosis, 2018, 277:80-89.*

Di Minno, M.N.D. et al. Carotid intima-media thickness in psoriatric arthritis: Differences between tumor necrosis factor-alpha blockers and traditional disedase-modifying antirheumatic drugs. Arterioscler. Thromb. Vasc. Biol., 2011, 31:705-712.*

Holdt, L.M., et al. Recent studies of the human chromosome 9p21 locus, which is associated with atherosclerosis in human populations. Arterioscler. Thromb. Vasc. Biol., 2012, 32:196-206.*

Helgadottir et al., "A common variant on chromosome 9p21 affects the risk of myocardial infarction", Jun. 8, 2007, Science, pp. 1491-1493, vol. 316, AAAS, Washington, DC.

McPherson et al., "A common allele on chromosome 9 associated with coronary heart disease", Jun. 8, 2007, Science, pp. 1488-1491, vol. 316, AAAS, Washington, DC.

Cunnington et al., "Genetic mechanisms mediating atherosclerosis susceptibility at the chromosome 9p21 locus", Jun. 2011, Curr Atheroscler Rep, pp. 193-201, vol. 13, Issue 3, Springer, Berlin, Germany.

Helgadottir et al., "The same sequence variant on 9p21 associates with myocardial infarction, abdominal aortic aneurysm and intracranial aneurysm", Feb. 2008, Nat Genet., pp. 217-224, vol. 40, Nature Publishing, London, United Kingdom.

Kojima et al., "CD47-blocking antibodies restore phagocytosis and prevent atherosclerosis", Nature, Jul. 20, 2016, pp. 86-90, vol. 536, No. 7614, Springer Nature, Basingstoke, United Kingdom.

Faruqi.,"Reactivating cellular rubbish removal ameliorates atherosclerosis: Cardiovascular disease", Nature Reviews, Drug Discovery, Aug. 19, 2016, pp. 602-603, vol. 15, No. 9, Springer Nature, Basingstoke, United Kingdom.

Narizhneva et al., "Thrombospondin-1 up-regulates expression of cell adhesion molecules and promotes monocyte binding to endothelium", The Faseb Journal, Apr. 15, 2005,pp. 1-24, vol. 19, No. 9, Faseb, Bethesda, MD.

Faruqi et al. (2016) "Reactivating cellular rubbish removal ameliorates atherosclerosis : Cardiovascular disease",pp. 602-603.

Kojima et al (2016) "CD47-blocking antibodies restore phagocytosis and prevent atherosclerosis",pp. 86-90.

Narizfineva: "Thrombospondin-1 up-regulates expression of cell adhesion molecules and promotes monocyte binding to endothelium",XP55350644,, 1158-1160.

* cited by examiner

CD47 expression is augmented by TNF-alpha

- Taken together:
  - Apoptosis reduces CD47 in SMCs (as previously shown)
  - But TNF blunts this decrement (new data)

CD47 expression in vascular disease

- CD47 is upregulated in human atherosclerotic plaque compared to normal vascular tissue Human microarray experiments performed in human plaque specimens. CP = carotid plaque. NA = non-atherosclerotic tissue FIG. 9
Correlation between CD47 and the TNF-α pathway
- Microarray datasets from human coronary artery samples – looking at members of the TNF superfamily
Athero vs no athero
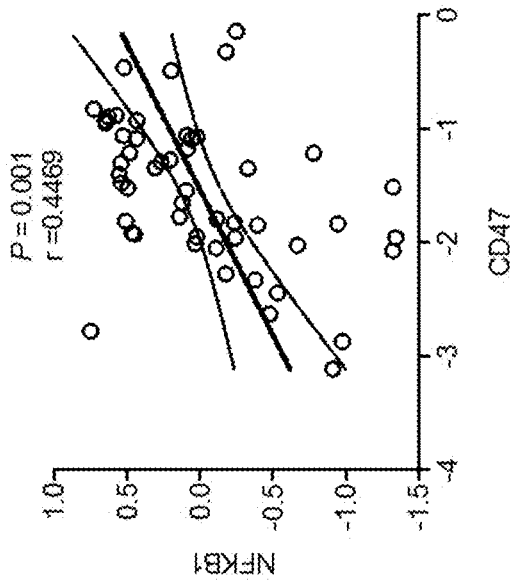
De novo athero vs in stent restenosis
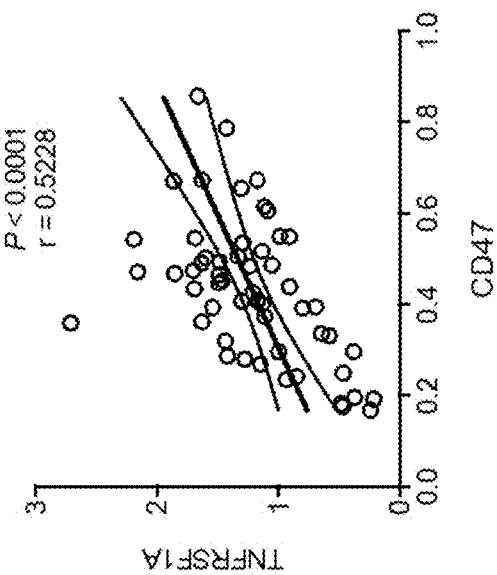

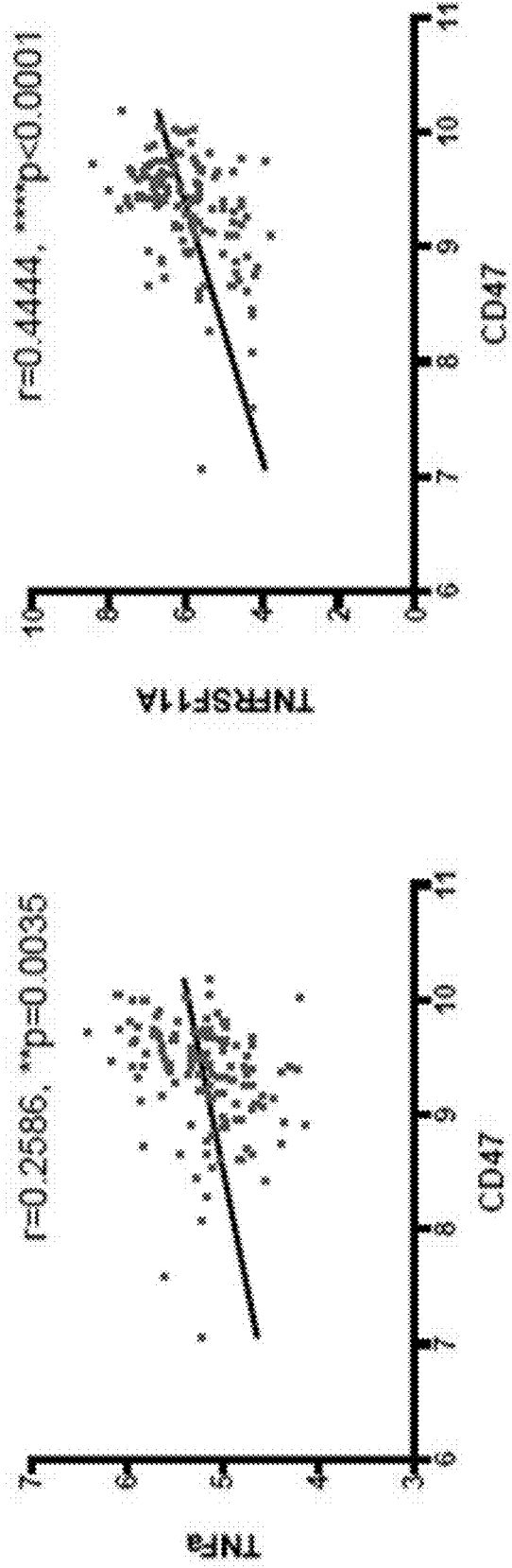

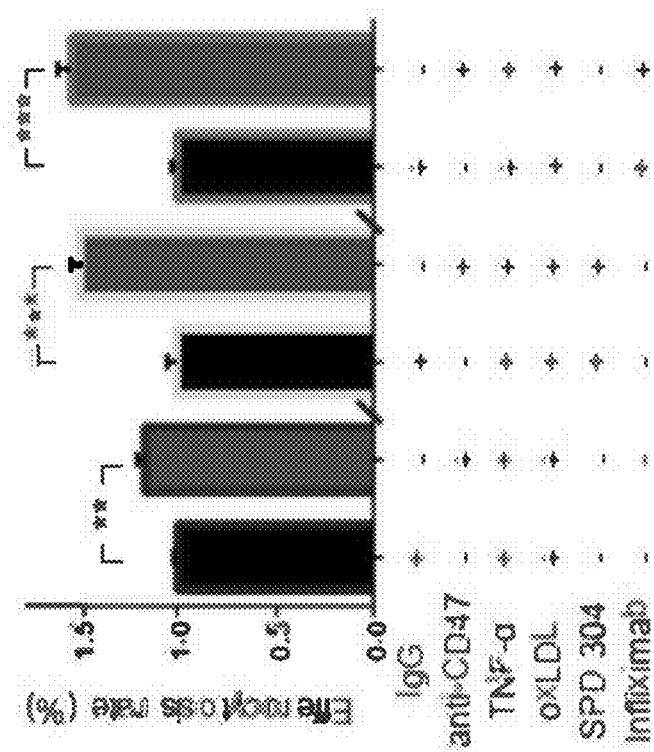
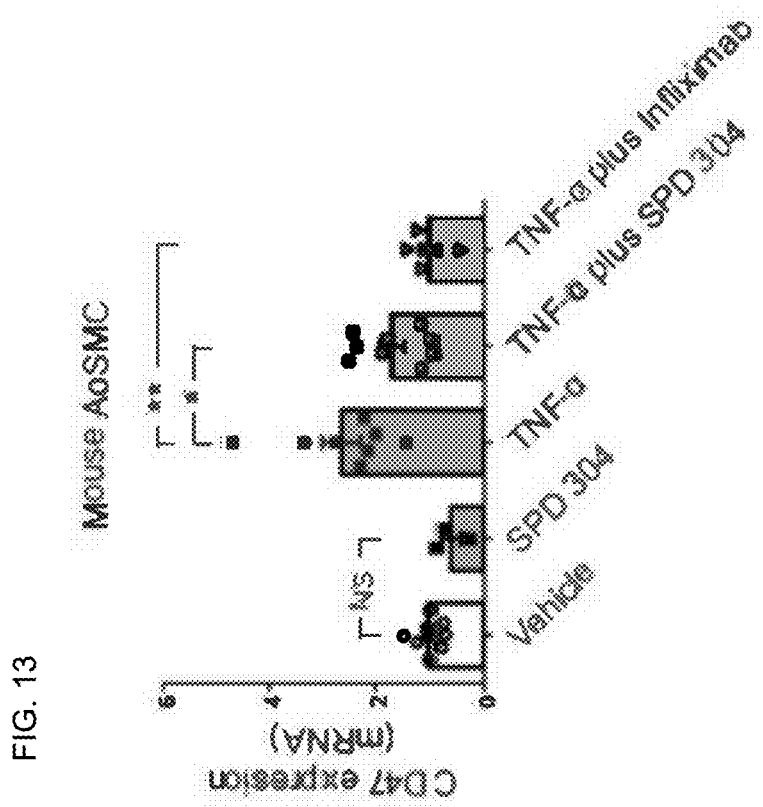
FIG. 13

SEQUENCE LISTING

```
<160> NUMBER OF SEQ ID NOS: 6

<210> SEQ ID NO 1
<211> LENGTH: 24
<212> TYPE: DNA
<213> ORGANISM: Homo sapiens

<400> SEQUENCE: 1
tggcaggggc gggcccaagg gctg                                              24

<210> SEQ ID NO 2
<211> LENGTH: 24
<212> TYPE: DNA
<213> ORGANISM: Homo sapiens

<400> SEQUENCE: 2
cagcccttgg gcccgcccct gcca                                              24

<210> SEQ ID NO 3
<211> LENGTH: 19
<212> TYPE: DNA
<213> ORGANISM: Homo sapiens

<400> SEQUENCE: 3
aggtccaatg gaaaaagac                                                    19

<210> SEQ ID NO 4
<211> LENGTH: 20
<212> TYPE: DNA
<213> ORGANISM: Homo sapiens

<400> SEQUENCE: 4
cagaaactgc tccttgaagt                                                   20

<210> SEQ ID NO 5
<211> LENGTH: 20
<212> TYPE: DNA
<213> ORGANISM: Homo sapiens

<400> SEQUENCE: 5
ccggaagcac ttctcctaga                                                   20

<210> SEQ ID NO 6
<211> LENGTH: 20
<212> TYPE: DNA
<213> ORGANISM: Homo sapiens

<400> SEQUENCE: 6
aagagagagc ggaagtgacg                                                   20
```

COMBINATION THERAPY FOR TREATMENT OF CORONARY ARTERY DISEASE

CROSS-REFERENCE

This application is a 371 application and claims the benefit of PCT Application No. PCT/US2016/019633, filed Feb. 25, 2016, which claims benefit of U.S. Provisional Patent Application No. 62/126,260, filed Feb. 27, 2015, which applications are incorporated by reference herein in their entirety.

GOVERNMENT SUPPORT

This invention was made with Government support under contract HL103605 awarded by the National Institutes of Health. The Government has certain rights in the invention.

INCORPORATION BY REFERENCE OF SEQUENCE LISTING PROVIDED AS A TEXT FILE

A sequence Listing is provided herewith a text file, S13-370_STAN-1065US2_Seqlist_ST25.txt, created on Mar. 23, 2016 and having a size of 2 KB. The contents of the text file are incorporated by reference herein in their entirety.

BACKGROUND OF THE INVENTION

Atherosclerotic cardiovascular disease (ASCVD) remains the primary cause of morbidity and mortality worldwide. Patients with ASCVD represent a heterogeneous group of individuals, with a disease that progresses at different rates and in distinctly different patterns. Despite appropriate evidence-based treatments for patients with ASCVD, recurrence and mortality rates remain 2-4% per year.

In general, atherosclerosis is believed to be a complex disease involving multiple biological pathways. Variations in the natural history of the atherosclerotic disease process, as well as differential response to risk factors and variations in the individual response to therapy, reflect in part differences in genetic background and their intricate interactions with the environmental factors that are responsible for the initiation and modification of the disease. Atherosclerotic disease is also influenced by the complex nature of the cardiovascular system itself where anatomy, function and biology all play important roles in health as well as disease.

Traditional risk factors account for approximately half of an individual's lifetime risk of cardiovascular disease. The balance, therefore, is accounted for by a combination of unmeasured environmental exposures and genetic factors. The recent advent of the genome-wide association study (GWAS) platform has made it possible to investigate the heritable component of complex polygenic disorders, such as atherosclerotic coronary artery disease (CAD). Using this approach, a region on chromosome 9p21.3 has repeatedly been identified in GWAS as the top locus for complex cardiovascular disease (Helgadottir et al. (2007) *Science* 316:1491-1493; McPherson et al. (2007) *Science* 316:1488-1491).

Available data suggest that the risk-associated polymorphisms: 1) are very common, with as much as a fifth of the world population carrying two copies of the risk allele (minor allele frequency ~50%) (Deloukas et al. (2013) Nat Genet 45:25-33); 2) are independent of all established risk factors, suggesting a novel mechanism of action (Cunnington and Keavney (2011) Curr Atheroscler Rep 13:193-201); 3) are responsible for up to 21% of the attributable risk of myocardial infarction (MI); and 4) promote risk across a spectrum of vascular diseases, including CAD, stroke, peripheral artery disease (PAD) and abdominal aortic aneurysm (AAA) (Helgadottir et al. (2008) *Nat Genet* 40:217-224).

Atherosclerotic plaque consists of accumulated intracellular and extracellular lipids, smooth muscle cells, connective tissue, and glycosaminoglycans. The earliest detectable lesion of atherosclerosis is the fatty streak, consisting of lipid-laden foam cells, which are macrophages that have migrated as monocytes from the circulation into the subendothelial layer of the intima, which later evolves into the fibrous plaque, consisting of intimal smooth muscle cells surrounded by connective tissue and intracellular and extracellular lipids.

SUMMARY OF THE INVENTION

Methods are provided for the prevention and treatment of coronary artery disease (CAD) in a subject, including without limitation methods of preventing or treating atherosclerosis. In the methods of the invention, an effective combined dose of an anti-CD47 agent and an anti-TNFα agent are administered to the subject in a dose and for a period of time effective to stabilize, prevent or reduce atherosclerotic plaque in the individual. In some embodiments the combined dosage provides for a synergistic response relative to the response obtained with either the anti-CD47 agent or the anti-TNFα agent delivered as a monotherapy. In some embodiments the effective dose of the anti-CD47 agent in the combined therapy is lower than the effective dose required as a monotherapy. In some embodiments the effective dose of the anti-TNFα agent in the combined therapy is lower than the effective dose required as a monotherapy.

In some embodiments, the subject is homozygous or heterozygous for a 9p21 risk allele. In some such embodiments the methods include genetic testing of the subject for the presence of a 9p21 risk allele. In other such embodiments the subject has been previously diagnosed for the presence of a 9p21 risk allele, where such methods may include, without limitation, analyzing a sample of genomic DNA from the individual for the presence of sequences of human chromosome 9p21 associated risk of CAD, including SNPs associated with the risk locus.

Another aspect of the present invention relates to the use of an effective combined dose of an anti-CD47 agent and an anti-TNFα agent in the manufacture of a medicament to stabilize, prevent or reduce atherosclerotic plaque, wherein the medicament is administered to an individual having or at risk of having atherosclerosis.

Still another aspect of the present invention provides a kit to stabilize, prevent or reduce atherosclerotic plaque. The kit includes an effective combined dose of an anti-CD47 agent and an anti-TNFα agent, in an amount sufficient to stabilize, prevent or reduce atherosclerotic plaque. The kit may also include reagents for genotyping at human chromosome 9p21, including alleles of rs10757278 and rs1333049. The kit may also instructions for use, reagents for monitoring atherosclerotic disease, and the like.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 9. Expression of CD47, TNFRSF1A and NFκB correlate in human atherosclerotic carotid endarterectomy samples.

FIG. 10. Expression of CD47 and TNFα correlate in human atherosclerotic coronary artery samples.

(FIG. 11A) Pro-atherosclerotic stimuli such as oxLDL and apoptotic stimuli (STS) induce the phagocytic clearance of smooth muscle cells (SMC). The presence of TNF-$\alpha$ blunts this increase in phagocytosis (FIG. 11B). Anti-CD47 Ab is disproportionately effective at promoting phagocytosis even in the presence of TNF-$\alpha$ (FIG. 11C).

FIG. 13. Mechanistic data showing that TNF inhibitors (SPD 304 and Infliximab) each reduce CD47 expression and synergize with anti-CD47 Ab to promote efferocytosis. A. Pretreatment of mouse vascular smooth muscle cells with a chemical inhibitor (SPD 304) or a monoclonal antibody (infliximab) directed against TNF-$\alpha$ prevents the increase in CD47 expression normally seen after TNFα exposure. B. The combination of these agents with anti-CD47 antibody therapy leads to a synergistic increase in efferocytosis with in vitro phagocytosis assays. \*\*\*=$p<0.001$, \*\*=$p<0.01$, \*=$p<0.05$.

DETAILED DESCRIPTION OF THE INVENTION

Figure 1:
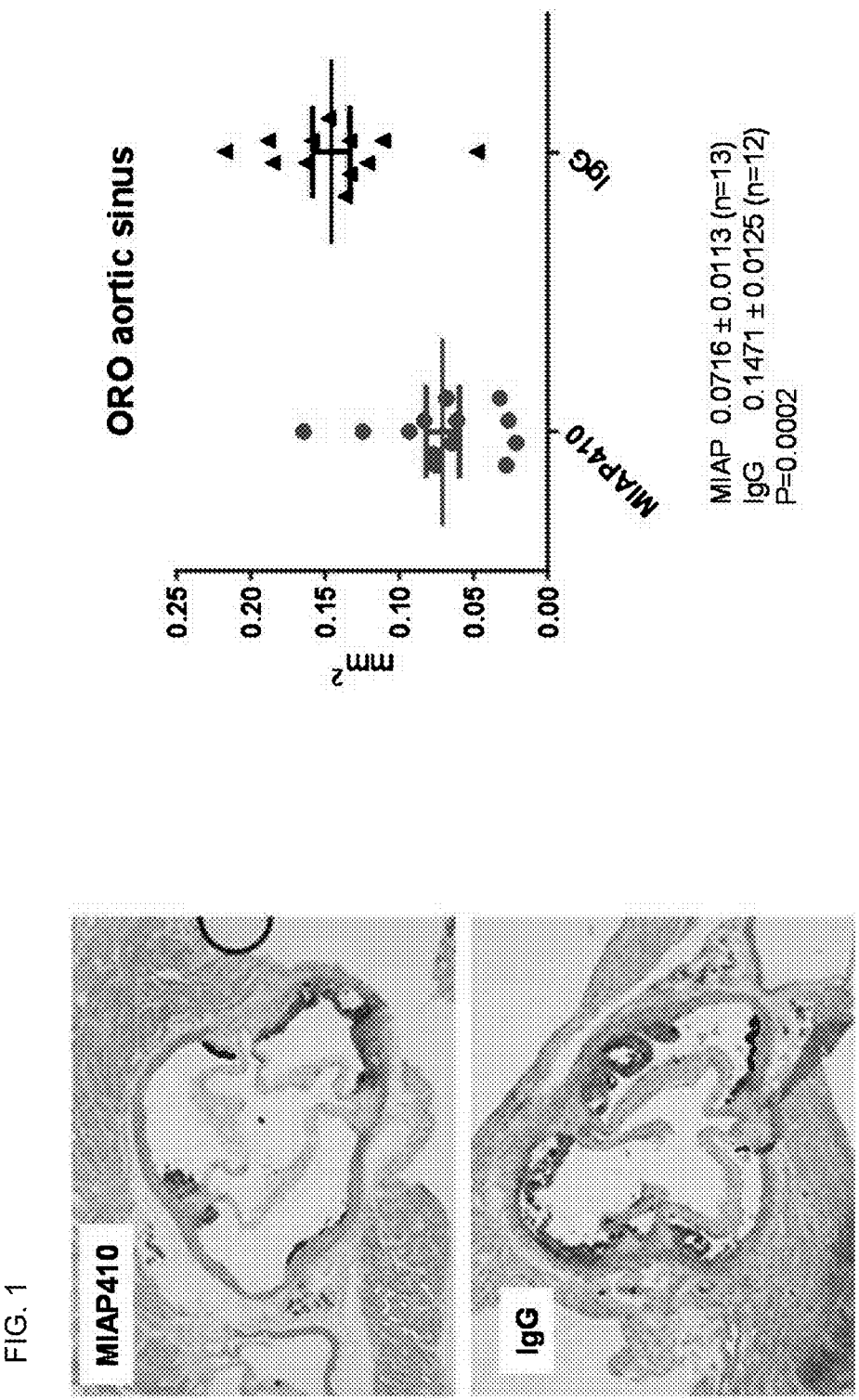
FIG. 1. Atherosclerotic plaque in the thoracic aorta is reduced by anti-CD47 Ab administration. Thoracic aortae from mice treated with anti-CD47 Ab (MIAP410) or control Ab (IgG) were harvested and pinned. Atherosclerotic plaque (white) area was quantified under low power microscopy in a blinded fashion. The percentage of the aortic vessel area covered by atherosclerotic plaque was quantified for each animal and is shown to be significantly reduced in animals which received anti-CD47 Ab.

The present invention relates to methods of treating a subject for atherosclerosis, including conditions such as CAD, peripheral artery disease (PAD) and cerebrovascular disease, by administering an effective combined dose of an anti-CD47 agent and an anti-TNFα agent. In some embodiments, the subject is homozygous or heterozygous for a 9p21 risk allele.

Coronary artery disease (CAD): is a narrowing or blockage of the arteries and vessels that provide oxygen and nutrients to the heart. It is caused by atherosclerosis, an accumulation of fatty materials on the inner linings of arteries. The resulting blockage restricts blood flow to the heart. When the blood flow is completely cut off, the result is a heart attack. CAD is the leading cause of death for both men and women in the United States.

Atherosclerosis (also referred to as arteriosclerosis, atheromatous vascular disease, arterial occlusive disease) as used herein, refers to a cardiovascular disease characterized by plaque accumulation on vessel walls and vascular inflammation. The plaque consists of accumulated intracellular and extracellular lipids, smooth muscle cells, connective tissue, inflammatory cells, and glycosaminoglycans. Inflammation occurs in combination with lipid accumulation in the vessel wall, and vascular inflammation is with the hallmark of atherosclerosis disease process.

Myocardial infarction is an ischemic myocardial necrosis usually resulting from abrupt reduction in coronary blood flow to a segment of myocardium. In the great majority of patients with acute MI, an acute thrombus, often associated with plaque rupture, occludes the artery that supplies the damaged area. Plaque rupture occurs generally in vessels previously partially obstructed by an atherosclerotic plaque enriched in inflammatory cells. Altered platelet function induced by endothelial dysfunction and vascular inflammation in the atherosclerotic plaque presumably contributes to thrombogenesis. Myocardial infarction can be classified into ST-elevation and non-ST elevation MI (also referred to as unstable angina). In both forms of myocardial infarction, there is myocardial necrosis. In ST-elevation myocardial infraction there is transmural myocardial injury which leads to ST-elevations on electrocardiogram. In non-ST elevation myocardial infarction, the injury is sub-endocardial and is not associated with ST segment elevation on electrocardiogram. Myocardial infarction (both ST and non-ST elevation) represents an unstable form of atherosclerotic cardiovascular disease. Acute coronary syndrome encompasses all forms of unstable coronary artery disease. Heart failure can occur as a result of myocardial dysfunction caused by myocardial infraction.

Angina refers to chest pain or discomfort resulting from inadequate blood flow to the heart. Angina can be a symptom of atherosclerotic cardiovascular disease. Angina may be classified as stable, which follows a regular chronic pattern of symptoms, unlike the unstable forms of atherosclerotic vascular disease. The pathophysiological basis of stable atherosclerotic cardiovascular disease is also complicated but is biologically distinct from the unstable form. Generally stable angina is not myocardial necrosis.

"Treatment", "treating", "treat" and the like are used herein to generally refer to obtaining a desired pharmacologic and/or physiologic effect. The effect can be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom. Those in need of treatment include individuals already diagnosed with CAD, e.g. atherosclerosis, as well as those in which the disease is to be prevented.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

An "effective amount" is an amount sufficient to effect beneficial or desired clinical results. An effective amount can be administered in one or more administrations. For purposes of this invention, an effective amount of an anti-CD47 agent combined with an anti-TNFα agent is an amount that is sufficient to palliate, ameliorate, stabilize, reverse, prevent, slow or delay the progression of the disease state, e.g. atherosclerosis or atherosclerotic plaque, by increasing phagocytosis of a target cell. For example, in an animal model the percent of aortic surface area with atherosclerotic plaque may be reduced 25%, 50%, 75% or more relative to a control treated animal. Similar effects may be obtained with indicia appropriate for human patients, including without limitation C-reactive protein [CRP] and fibrinogen; lipoprotein-associated phospholipase A2 [Lp-PLA2] and myeloperoxidase [MPO]; growth differentiation factor-15 [GDF-15]) inflammatory markers; ambulatory arterial stiffness, IVUS imaging, and the like. See, for example Krintus et al. (2013) Crit Rev Clin Lab Sci. 11:1-17; Kollias et al. (2012) Atherosclerosis 224(2):291-301; and Kollias et al. (2011) Int. J. Cardiovasc. Imaging 27(2):225-37, each herein specifically incorporated by reference.

Tumor necrosis factor alpha (TNF-α) is a pro-inflammatory cytokine produced by macrophages and lymphocytes that mediates inflammation in a number of conditions. The strategies for inhibiting TNF that have been most extensively studied to date consist of monoclonal anti-TNFα antibodies, anti-TNF receptor antibodies, and soluble TNF receptors (sTNF-R). Some specific examples of anti-TNF agents that are in current clinical use are listed below.

Infliximab (IFX) is a recombinant IgG1 monoclonal antibody specific for TNF-α that hinders the cytokine from triggering the cellular TNF receptor complex. IFX needs to be administered by intravenous infusion and has a terminal half-life of 8-10 days. Conventionally it is administered every 4-8 weeks and the dosage varies from 3 to 6 (to 10) mg/kg. Combination therapies of the present invention may use a dose or dosing schedule that provides for a lower dose or reduced dosing schedule relative to conventional schedules.

Adalimumab is a monoclonal antibody of recombinant immunoglobulin (IgG1) containing only human sequences of peptides. It is an antagonist of TNF-α, which is able to prevent the binding of TNF-α to its receptors. It has a half-life of 10-20 days. The conventional dose of ADA is 25 mg s.c. twice a week. Combination therapies of the present invention may use a dose or dosing schedule that provides for a lower dose or reduced dosing schedule relative to conventional schedules.

Golimumab is a human anti-TNF-α monoclonal antibody that is generated and matured in an in vivo system. GOLI has a high affinity and specificity for human TNF-α and effectively neutralizes TNF-α bioactivity in vitro. Conventional dosing is from 50 to 100 mg. Combination therapies of the present invention may use a dose or dosing schedule that provides for a lower dose or reduced dosing schedule relative to conventional schedules.

Etanercept is a genetically engineered protein comprising two molecules of the extracellular domain of TNF receptor II (p75) and the Fc portion of IgG1. Due to its half-life of 3-5.5 days, ETN is conventionally administered subcutaneously (s.c), either on a weekly basis (50 mg) or twice a week (25 mg). Combination therapies of the present invention may use a dose or dosing schedule that provides for a lower dose or reduced dosing schedule relative to conventional schedules.

Certolizumab is a pegylated anti-TNF-alpha monoclonal antibody. Certolizumab is a humanized antibody fragment (Fab) that is attached to polyethylene glycol to allow for less frequent administration. Certolizumab has a high affinity for human TNF-alpha, selectively targeting TNF-alpha in inflamed tissue. Although the presence of a Fab' portion allows certolizumab to retain the potency of the entire antibody, certolizumab is unable to bind phagocytic cells or to lyse cells because of a lack of an Fc portion. The elimination half-life of certolizumab was demonstrated to be 311 hours.

CD47, also known as integrin associated protein (IAP) is a 50 kDa membrane receptor that has extracellular N-terminal IgV domain, five transmembrane domains, and a short C-terminal intracellular tail transmembrane, belonging to the immunoglobulin superfamily, with interacts with integrins, most commonly integrin $\alpha v \beta 3$, thrombospondin-1 (TSP-1) and signal-regulatory protein alpha (SIRPα). The reference sequence for the human mRNA has the Genbank accession number NM_001025079, and the protein reference sequence is NP_001768.

The CD47/SIRPα interaction leads to bidirectional signaling, resulting in different cell-to-cell responses including inhibition of phagocytosis, stimulation of cell-cell fusion, and T-cell activation As used herein, the term "anti-CD47 agent" refers to any agent that reduces the binding of CD47 (e.g., on an affected cell) to SIRPα (e.g., on a phagocytic cell). In some embodiments the anti-CD47 agent does not interfere or bind to the regions of CD47 that bind to thrombospondin. In some embodiments, the anti-CD47 agent does not activate CD47 upon binding. When CD47 is activated, a process akin to apoptosis (i.e., programmed cell death) occurs (Manna and Frazier, Cancer Research, 64, 1026-1036, Feb. 1 2004). Thus, in some embodiments, the anti-CD47 agent does not directly induce cell death of a CD47-expressing cell.

Non-limiting examples of suitable anti-CD47 reagents include high affinity SIRPα reagents, anti-SIRPα antibodies, and anti-CD47 antibodies or antibody fragments. In some embodiments, a suitable anti-CD47 agent (e.g. an anti-CD47 antibody, a high affinity SIRPα reagent, etc.) specifically binds CD47 to reduce the binding of CD47 to SIRPα. In some embodiments, a suitable anti-CD47 agent (e.g., an anti-SIRPα, antibody, etc.) specifically binds SIRPα to reduce the binding of CD47 to SIRPα. A suitable anti-CD47 agent that binds SIRPα does not activate SIRPα (e.g., in the SIRPα-expressing phagocytic cell).

The efficacy of a suitable anti-CD47 agent can be assessed by assaying the agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 160%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In one embodiment of the invention, the anti-CD47 agent, or a pharmaceutical composition comprising the agent, is provided in an amount effective to detectably inhibit the binding of CD47 to SIRPα present on the surface of phagocytic cells. The effective amount is determined via empirical testing routine in the art, for example in a biological sample taken from an infected individual. The effective amount may vary depending on the number of cells being targeted, the location of the cells, and factors specific to the subject.

High affinity SIRPα reagent. In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules.

A suitable high affinity SIRPα reagent reduces (e.g., blocks, prevents, etc.) the interaction between the native proteins SIRPα and CD47. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of infected cells over non-infected cells. Those cells that express higher levels of CD47 (e.g., infected cells) relative to other cells (non-infected cells) will be preferentially phagocytosed. Thus, a suitable anti-SIRPα antibody specifically binds SIRPα without activating/stimulating enough of a signaling response to inhibit phagocytosis.

Suitable antibodies include fully human, humanized or chimeric versions of such antibodies. Humanized antibodies are especially useful for in vivo applications in humans due to their low antigenicity. Similarly caninized, felinized, etc antibodies are especially useful for applications in dogs, cats, and other species respectively.

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Comparable: As used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: A "composition" or a "pharmaceutical composition" according to this invention refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing Regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations. The definition also includes sample that have been enriched for particular types of molecules, e.g., nucleic acids, polypeptides, etc.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides; high affinity binding of a SIRPα polypeptide to CD47; etc.) In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 (i.e., anti- CD47 agents), or that otherwise block the interaction between CD47 and SIRPα, agents that bind to calreticulin or its LRP receptor, etc.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural protein.

A "fusion" polypeptide is a polypeptide comprising a polypeptide or portion (e.g., one or more domains) thereof fused or bonded to heterologous polypeptide. A fusion soluble CRT protein, for example, will share at least one biological property in common with a native sequence soluble CRT polypeptide. Examples of fusion polypeptides include immunoadhesions, as described above, which combine a portion of the polypeptide of interest with an immunoglobulin sequence, and epitope tagged polypeptides, which comprise a soluble polypeptide of interest or portion thereof fused to a "tag polypeptide". The tag polypeptide has enough residues to provide an epitope against which an antibody can be made, yet is short enough such that it does not interfere with biological activity of the polypeptide of interest. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. For example, derivatives and fusion of soluble CRT find use as CRT mimetic molecules.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

9p21 Risk. As used herein, the term "an individual carrying at least one 9p21 risk factor" refers to humans in which one or more risk alleles at the 9p21 locus are present in the genome. Such individuals have been shown to have an increased risk of: early onset myocardial infarction, abdominal aortic aneurysm, stroke, peripheral artery disease, and myocardial infarction/coronary heart disease. This risk is independent of traditional risk factors, including diabetes, hypertension, cholesterol, and obesity. See, for example, Helgadottir et al. Science. 2007; 316(5830):1491-1493; Helgadottir et al. Nat Genet. 2008; 40(2):217-224; Palomaki et al. JAMA. 2010; 303(7):648-656; and Roberts et al. Curr Opin Cardiol. 2008; 23:629-633, each herein specifically incorporated by reference.

The 9p21 locus is in tight LD (linkage disequilibrium), and a number of single nucleotide polymorphisms (SNP) markers have been shown to be useful in diagnosis. Representative SNPs include without limitation rs10757278; rs3217992; rs4977574; rs1333049; rs10757274; rs2383206; rs2383207; Rs3217989; rs1333040; rs2383207; rs10116277; rs7044859; rs1292136; rs7865618; rs1333045; rs9632884; rs10757272; rs4977574; rs2891168; rs6475606; rs1333048; rs1333049; Rs1333045; etc.

Efferocytosis. The process by which professional and nonprofessional phagocytes dispose of apoptotic cells in a rapid and efficient manner. Efferocytosis involves a number of molecules, including ligands on the apoptotic cells, e.g. phosphatidylserine; receptors on the efferocyte; soluble ligand-receptor bridging molecules; and so-called "find-me" and "don't-eat-me" molecules, e.g., lysosphospholipids and CD47, the expression of which by dying cells is altered to attract nearby phagocytes. By clearing apoptotic cells at a relatively early stage of cell death, when the cell plasma and organelle membranes are still intact, postapoptotic, or "secondary", necrosis is prevented. Prevention of cellular necrosis, in turn, prevents the release of potentially damaging intracellular molecules into the extracellular milieu, including molecules that can stimulate inflammatory, proatherosclerotic and/or autoimmune responses.

The efficiency of efferocytic clearance in atherosclerotic lesions plays a key role in disease development. Efferocytosis is known to be impaired in human atherosclerotic plaque. A prominent feature of advanced atherosclerotic lesions is the necrotic core, or lipid core, which is a collection of dead and necrotic macrophages surrounded by inflammatory cells. Necrotic cores are thought to be a major feature responsible for plaque "vulnerability", i.e., plaques capable of undergoing disruption and triggering acute luminal thrombosis. Plaque disruption and acute thrombosis are the events that trigger acute coronary syndromes, including myocardial infarction, unstable angina, sudden cardiac death, and stroke.

By "manipulating efferocytosis" is meant an up-regulation or a down-regulation in efferocytosis of a targeted cell, e.g. apoptotic SMC, by at least about 10%, or up to 20%, or 50%, or 70% or 80% or up to about 90% compared to level of efferocytosis observed in absence of intervention.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells. However, "non-professional" cells are also known to participate in efferocytosis, such as neighboring SMCs in the blood vessel wall.

Methods

Methods are provided for treating or reducing atherosclerosis by administering an effective combined dose of an anti-CD47 agent and an anti-TNFα agent to increase efferocytosis of cellular components of coronary or extracardiac plaque, including the efferocytosis of apoptotic smooth muscle cells. Administration may be simultaneous or concomitant, where the dosing schedule may be tailored to each of the agents in the combination. As an example, a weekly dosing of the anti-TNFα agent may be concomitant with a semi-weekly, or bi-weekly dosing of the anti-CD47 agent, or vice versa. Methods of administration to the cardiovascular system are of particular interest.

Effective doses of the therapeutic entity of the present invention vary depending upon many different factors, including the nature of the agent, means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage can range from about 0.0001 to 500 mg/kg, and more usually 0.01 to 100 mg/kg, of the host body weight. For example dosages can be 1 mg/kg body weight or 10 mg/kg body weight or within the range of 1-50 mg/kg. The dosage may be adjusted for the molecular weight of the reagent and may be reduced relative to the dosage required for a monotherapy of either agent in the combination. An exemplary treatment regime entails administration daily, semi-weekly, weekly, once every two weeks, once a month, etc. In another example, treatment can be given as a continuous infusion. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient. It will be understood by one of skill in the art that such guidelines will be adjusted for the molecular weight of the active agent, e.g. in the use of polypeptide fragments, in the use of antibody conjugates, in the use of high affinity SIRPα reagents, etc. The dosage may also be varied for localized administration, e.g. intranasal, inhalation, etc., or for systemic administration, e.g. i.m., i.p., i.v., and the like.

For the treatment of disease, the appropriate dosage of the agent will depend on the severity and course of the disease, whether the agent is administered for preventive purposes, previous therapy, the patient's clinical history and response to the antibody, and the discretion of the attending physician. The agent is suitably administered to the patient at one time or over a series of treatments.

Suitable agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the effective combined dose of an anti-CD47 agent and an anti-TNFα agent are further combined with a third therapeutic agent, e.g., drugs useful in the treatment of atherosclerosis. Such combinations may include, without limitation, statins. Statins are inhibitors of HMG-CoA reductase enzyme. These agents are described in detail; for example, mevastatin and related compounds as disclosed in U.S. Pat. No. 3,983,140; lovastatin (mevinolin) and related compounds as disclosed in U.S. Pat. No. 4,231,938; pravastatin and related compounds as disclosed in U.S. Pat. No. 4,346,227; simvastatin and related compounds as disclosed in U.S. Pat. Nos. 4,448,784 and 4,450,171; fluvastatin and related compounds as disclosed in U.S. Pat. No. 5,354,772; atorvastatin and related compounds as disclosed in U.S. Pat. Nos. 4,681,893, 5,273,995 and 5,969,156; and cerivastatin and related compounds as disclosed in U.S. Pat. Nos. 5,006,530 and 5,177,080. Additional agents and compounds are disclosed in U.S. Pat. Nos. 5,208,258, 5,130,306, 5,116, 870, 5,049,696, RE 36,481, and RE 36,520. Statins include the salts and/or ester thereof.

Therapeutic formulations comprising one or more agents of the invention are prepared for storage by mixing the agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the agent to be administered will be governed by such considerations, and is the minimum amount necessary to treat or prevent atherosclerosis.

The agent can be administered by any suitable means, including topical, oral, parenteral, subcutaneous, intraperitoneal, intrapulmonary, and intranasal. Parenteral infusions include intramuscular, intravenous, intraarterial, intraperitoneal, intrathecal or subcutaneous administration. In addition, the agent can be suitably administered by pulse infusion, particularly with declining doses of the agent.

The combination of agents may be used in the same dosages and with administration routes as used hereinbefore as individual agents, or about from 1, 5, 10, 15, 20, 25, 30, 35, 40, 45, 50, 55, 60, 65, 70, 75, 80, 85 90, 95, to 99% of the heretofore employed dosages.

An agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent by non-covalent associations, such as non-covalent bonding or by encapsulation. The nature of the carrier can be either soluble or insoluble for purposes of the invention. Those skilled in the art will know of other suitable carriers for binding anti-CD47 agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the anti-CD47 agent through an acceptable chemical linker or chelation carrier. Positron emitting moieties for use in the present invention include $^{18}F$, which can be easily conjugated by a fluorination reaction with the agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Cell-based systems may be used to identify compounds and combinations of compounds that act to ameliorate cardiovascular disease symptoms. For example, such cell systems may be exposed to a combination of agents compound at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype.

In addition, animal-based disease systems, such as those described, above may be used to identify compounds capable of ameliorating disease symptoms. Such animal models may be used as test substrates for the identification of drugs, pharmaceuticals, therapies, and interventions, which may be effective in treating disease. For example, animal models may be exposed to a compound, suspected of exhibiting an ability to ameliorate cardiovascular disease symptoms, at a sufficient concentration and for a time sufficient to elicit such an amelioration of disease symptoms in the exposed animals. The response of the animals to the exposure may be monitored by assessing the reversal of disorders associated with disease, for example, by counting the number of atherosclerotic plaques and/or measuring their size before and after treatment.

With regard to intervention, any treatments that reverse any aspect of cardiovascular disease symptoms should be considered as candidates for human disease therapeutic intervention. Dosages of test agents may be determined by deriving dose-response curves.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention now being fully described, it will be apparent to one of ordinary skill in the art that various changes and modifications can be made without departing from the spirit or scope of the invention.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLE 1

It has been estimated that as many as one million cells undergo programmed cell death per second each day in the human body. Despite the frequency of this event, apoptotic cells are rarely observed in vivo, even in organs with high basal turnover rates such as the bone marrow or thymus. This observation is attributed to the fact that apoptotic bodies are rapidly and efficiently cleared by both professional (i.e. macrophage) and non-professional (i.e. neighboring cell) phagocytes. Previously considered an obligate homeostatic event, the process of 'efferocytosis' (from the Greek: to carry the dead to the grave) is now appreciated to occur as the result of highly orchestrated paracrine signaling between the AB and its potential phagocyte. During programmed cell death, apoptosing cells secrete chemotactic "find-me" ligands, upregulate cell-surface "eat-me" ligands, and repress inhibitory "don't-eat-me" signals. Remarkably, this process occurs in an "immunologically silent" manner, where the successful execution of the engulfment process triggers an anti-inflammatory cytokine profile from the phagocyte, presumably as a signal that no further immune activation is required. Conversely, apoptotic cells which evade clearance rapidly become secondarily necrotic and induce an inflammatory 'danger response' as they release toxic and antigenic intracellular content which was previously sequestered. Impaired efferocytosis is now recognized as a major driver of autoimmune, inflammatory and malignant disorders, where failed immune surveillance is thought to result from an imbalance in the pro- and anti-phagocytosis signatures on target cells.

Atherosclerosis is a condition in which apoptosis is dramatically accelerated. Complicating this is the fact that efferocytosis may be reduced by nearly ~20-fold as the human atherosclerotic plaque develops. The reason for this defect is not clear, but is likely related in part to competition for phagocyte receptors by oxidized LDL and/or the generation of autoantibodies which mask important cell-surface ligands on the apoptotic body. Moreover, experimental atherosclerosis models can be significantly accelerated by inhibiting the expression of 'eat-me' ligands in mice, and these animals display lesions with advanced necrotic cores replete with apoptotic corpses. Impaired efferocytosis likely has important clinical consequences in atherogenesis, given that delayed clearance of dying SMCs has been linked to vascular inflammation and matrix destabilization, and that residual necrotic debris frequently localizes to regions of the lesion most susceptible to rupture. The fact that loss of Cdkn2b in mice increases the size of the plaque and its lipid core while reducing the thickness and stability of the fibrous cap may partially explain the simultaneous link in humans between 9p21 and both total CAD burden and acute clinical events, such as myocardial infarction. Impaired efferocytosis may also promote atherosclerosis secondarily through the phagocyte.

Emerging evidence has revealed that the phenotype of the apoptosing cell can have a dramatic impact on the behavior of the nearby macrophage and its ultimate capacity to maintain lipid homeostasis. Under physiological conditions, macrophages which have successfully engaged an apoptotic body upregulate transmembrane export pathways downstream of LRP-1 and a variety of nuclear receptors, presumably in preparation for the impending doubling of their intracellular content. A key effector molecule in this pathway is ABCA1, which promotes reverse cholesterol efflux and is important for limiting the local accumulation of cholesterol in the fatty streak. In the current study, macrophages presented with CDKN2B-deficient apoptotic bodies failed to activate this pathway and could not process oxidized lipids efficiently. Mechanistically, this likely occurred because CDKN2B-deficient cells express low levels of CALR, which is a well described ligand for the LRP-1 receptor. As a consequence, these otherwise healthy macrophages displayed a blunted increase in ABCA1 expression and were more likely to differentiate into foam cells—a process which is recognized as maladaptive and pro-atherosclerotic. Thus, while the efferocytic capacity of the phagocyte is not altered by its basal CDKN2B expression, its ultimate participation in the atherogenesis process is highly dependent on whether it encounters a 'normal' AB, or one that has been rendered 'inedible' due to a lack of CDKN2B.

CDKN2B mediates its phagocytic effects through calreticulin. Calreticulin is an evolutionarily conserved 46 kD chaperone protein which regulates a variety of cellular functions including calcium homeostasis, cell adhesion, wound healing, immunity, fibrosis and the response to stress. Additionally, CALR has been implicated as one of the major regulators of efferocytosis, and is a critical engulfment ligand which is absolutely required for phagocytic clearance. During apoptosis, CALR co-localizes to the surface of the AB with exposed phosphatidylserine and activates LRP-1 on the surface of the adjacent macrophage. Interestingly, prior studies have shown that mice deficient in this CALR receptor phenocopy several aspects of the CDKN2B-deficient mouse, including the propensity to develop large aortic aneurysms and advanced lipid-laden atherosclerotic plaques, with no difference in plasma lipoprotein levels (reviewed in Boucher and Herz (2011) *Biochem Pharmacol* 81:1-5). Further, CALR has also been identified as a key regulator of tumor surveillance and the clearance of malignant cells.

Because the 9p21 locus promotes risk independently of all classical risk factors, a therapy that promotes efferocytosis can provide incremental benefit beyond antihypertensives, antidiabetics and lipid lowering therapies.

Figure 2:
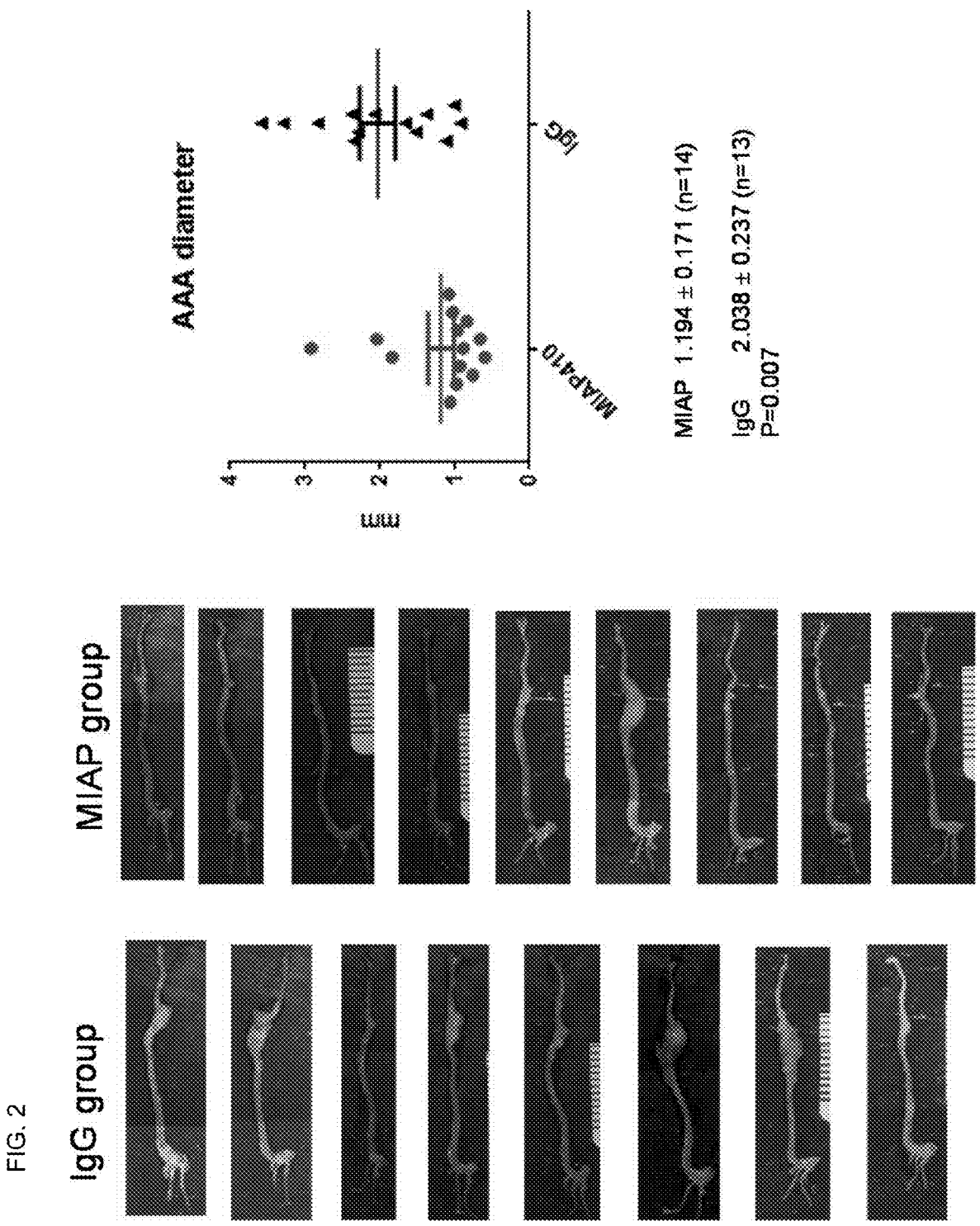
FIG. 2. Representative explanted aortas from control Ab treated mice (IgG) reveal a high incidence of aneurysms after angiotensin infusion. Representative explanted aortas from antiCD47 Ab treated mice (MIAP410) reveal a low incidence of aneurysms after angiotensin infusion. The graph depicts data points for anti-CD47 Ab treatment reducing aneurysm size.
Figure 3:
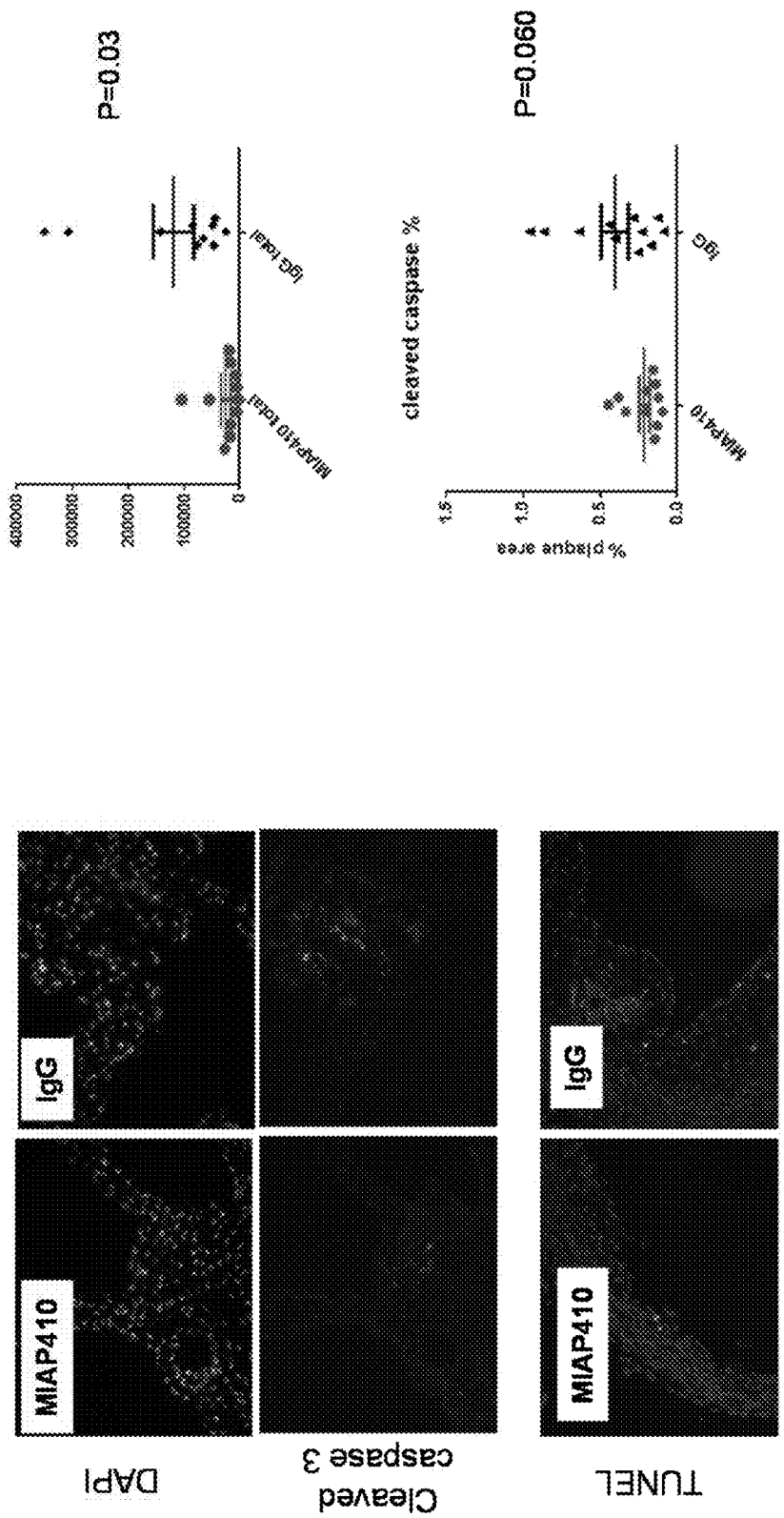
FIG. 3. Staining with DAPI, for cleaved caspase, and Tunel. The graphs illustrate a decrease in the number of apoptotic cells with anti-CD47 treatment, as evidenced by staining for cleaved caspase 3. The cleaved caspase % has a $p<0.05$. The TUNEL staining is confirmatory.
Figure 4:
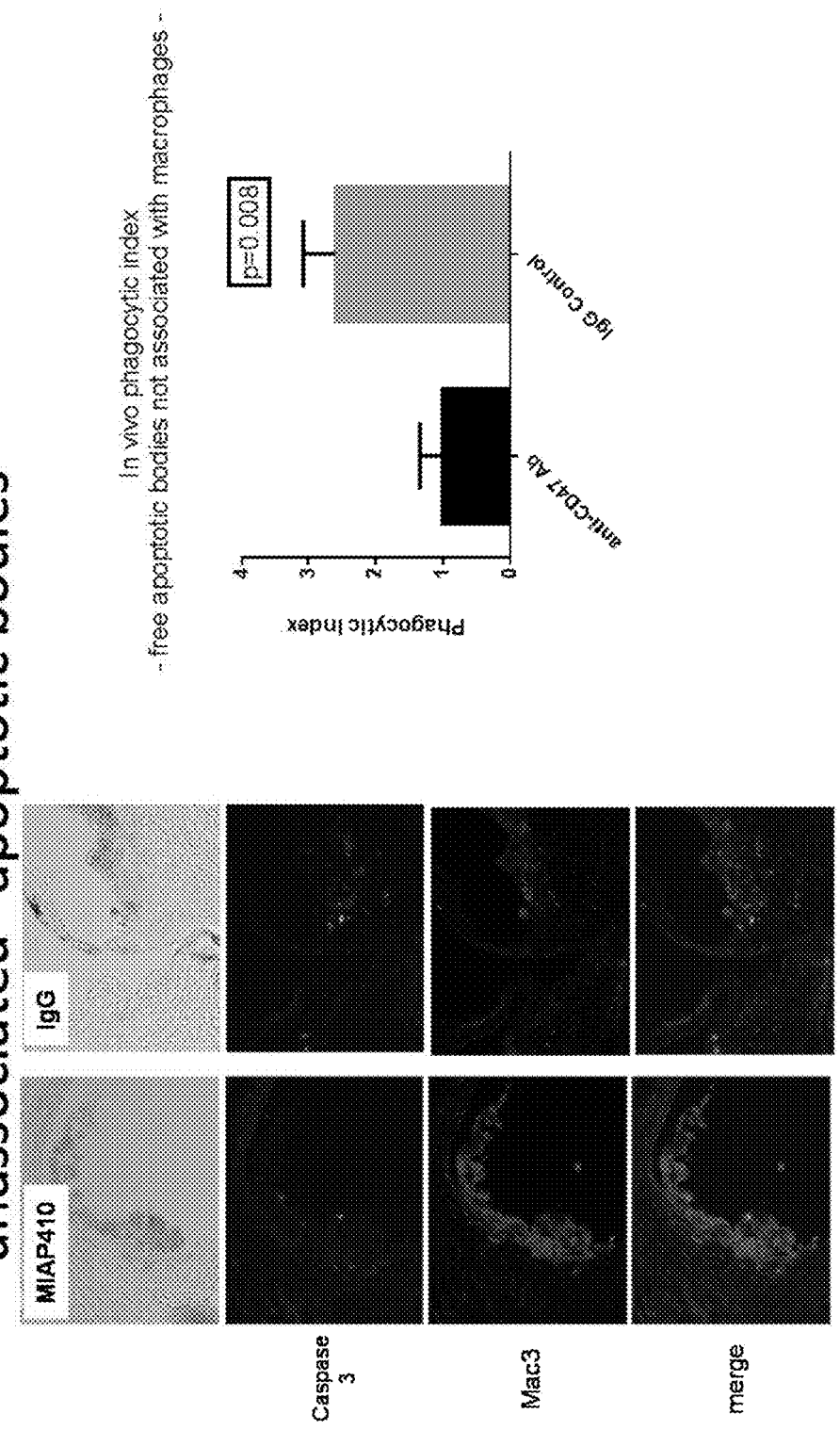
FIG. 4. The in vivo phagocytic index associated with atherosclerosis is increased by treatment with anti-CD47, as illustrated by a decrease in the number of free apoptotic bodies not associated with macrophages.

Our data demonstrates that therapies that promote phagocytosis and/or efferocytosis (including but not limited to anti-CD47 Ab therapy) dramatically reduce atherosclerosis, as shown in FIG. 1 and aneurysm disease, as shown in FIG. 2 We have shown that such therapies reduce the number of apoptotic cells present in the developing vascular lesion, shown in FIG. 3, even though they have no direct effect on programmed cell death or apoptosis itself, in vitro. Using both in vitro and in vivo assays (shown in FIGS. 3 and 4), we have confirmed that anti-CD47 Ab therapy stimulates the phagocytosis/efferocytosis of vascular cells, which therefore accounts for the reduced number of apoptotic cells in the atherosclerotic plaque, and consequently accounts for the reduced size of the atherosclerotic lesion.

Figure 5:
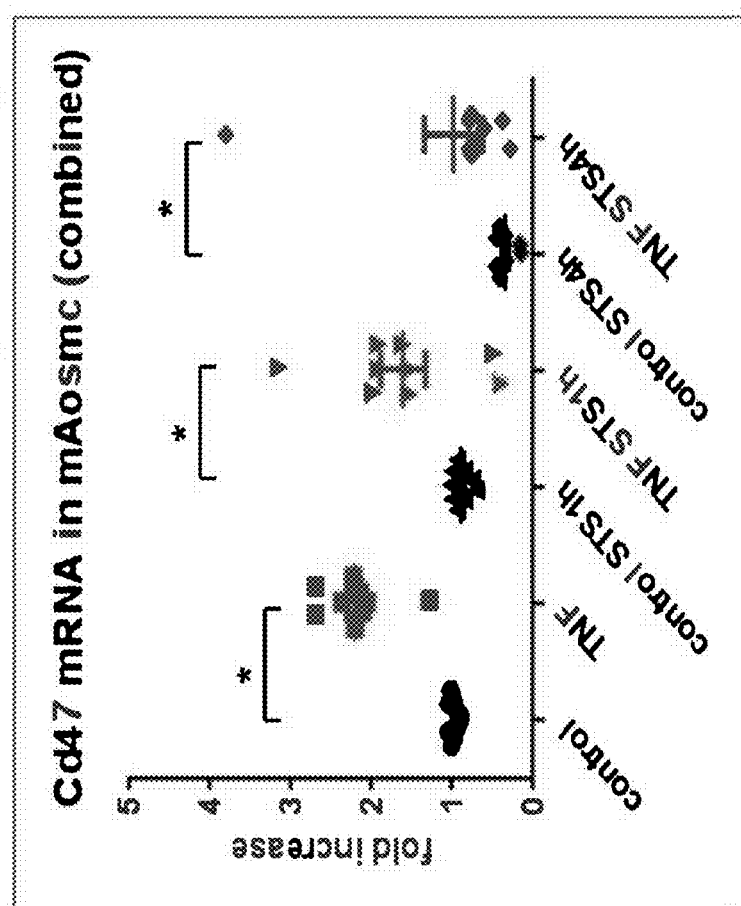
FIG. 5. CD47 expression is augmented by TNF-$\alpha$, which blunts the reduction of CD47 expression in smooth muscle cells due to apoptosis.
Figure 6:
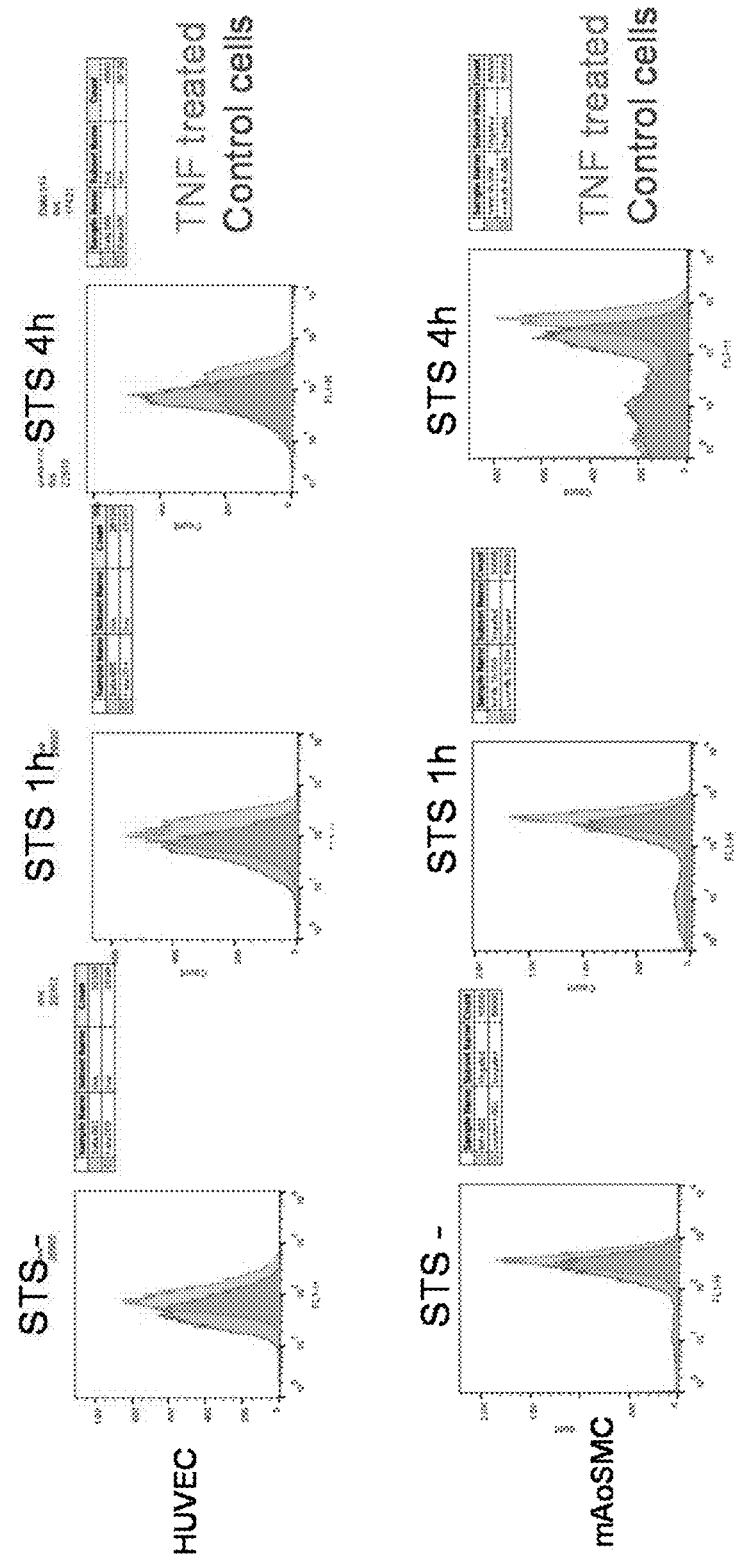
FIG. 6. Graphs depicting cell surface CD47 expression in HUVEC and mAoSMC in the absence and presence of TNF-$\alpha$.

To understand why anti-CD47 Ab therapy is so potent in the vascular lesion, we treated vascular cells with the pro-atherosclerotic cytokine, TNF-alpha, and found that this agent blunted the expected decrease in CD47 mRNA expression that occurs during cellular stress and/or apoptosis over time (FIG. 5, STS=staurosporine). Similarly, TNF-alpha treatment blunted the apoptosis-induced reduction in cell-surface expression of CD47 on vascular cells (FIG. 6). Because TNF-alpha is known to be expressed in the atherosclerotic plaque, and we now show that TNF-alpha upregulates expression of the anti-phagocytic CD47 molecule, these data explain why diseased vascular cells become resistant to phagocytosis/efferocytosis in vascular disease.

Figure 7:
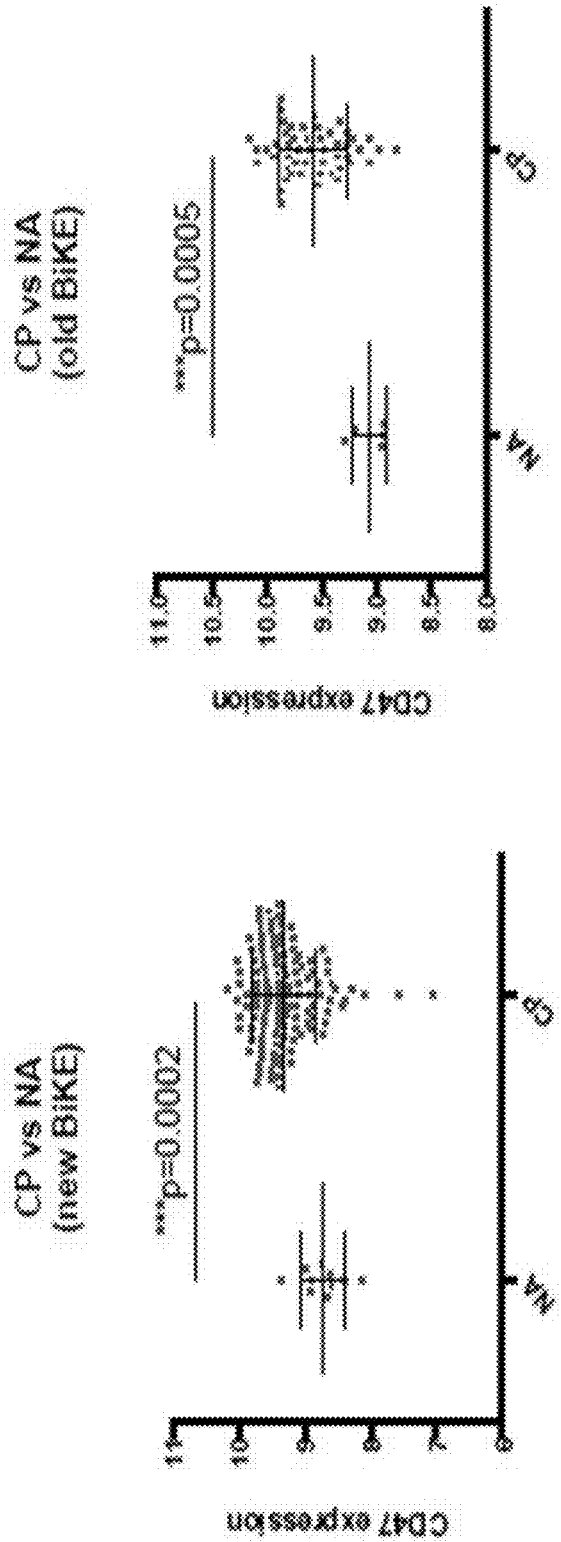
FIG. 7. CD47 is upregulated in human atherosclerotic plaque compared to normal vascular tissue.
Figure 8:
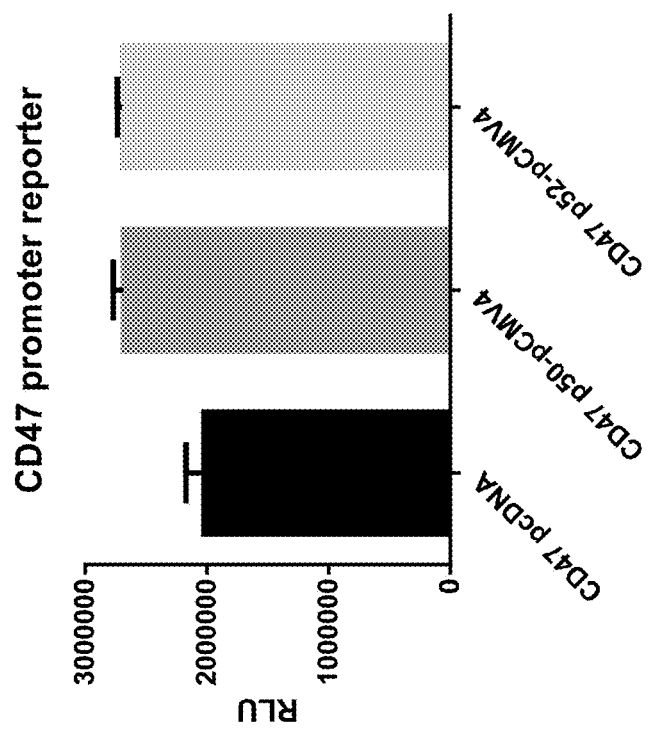
FIG. 8. Overexpression of NF-κB subunits, including NFκB1 activate expression of CD47.

We confirm that CD47 expression is upregulated in human atherosclerotic tissue relative to non-atherosclerotic tissue (FIG. 7) and confirm that it is specifically upregulated within the atherosclerotic plaque in human lesions. Signaling studies confirm that the CD47 promoter contains predicted transcription factor binding sites for molecules known to be downstream of TNF-alpha. Luciferase reporter assays confirm that overexpression of a representative TNF-alpha effector molecule, NFKB1, leads to CD47 expression in vascular cells, confirming the mechanism of action (FIG. 8). Microarray assays reveal that CD47 expression is positively correlated with NFKB1 in human coronary artery samples (FIG. 9, right) and TNF-alpha in human carotid plaque samples (FIG. 10, left), confirming the association in human tissue.

Figure 11A:
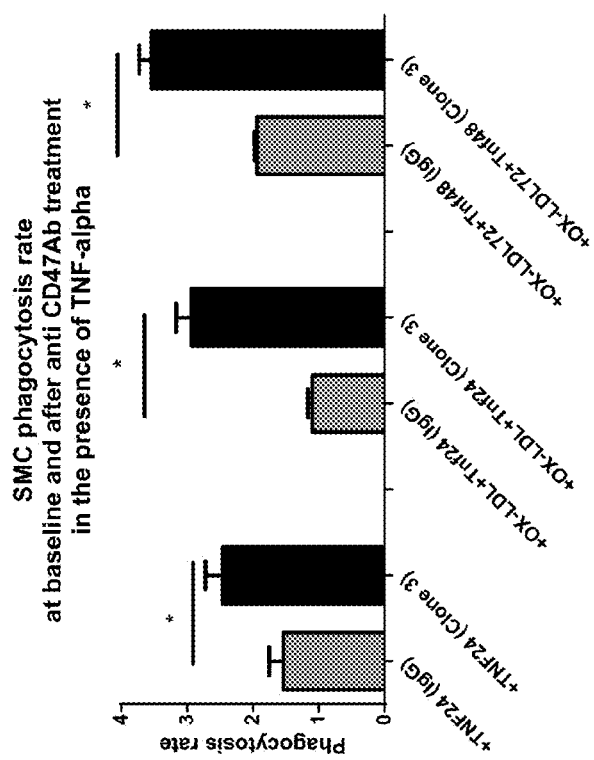
FIG. 11A-11C.
Figure 11B:
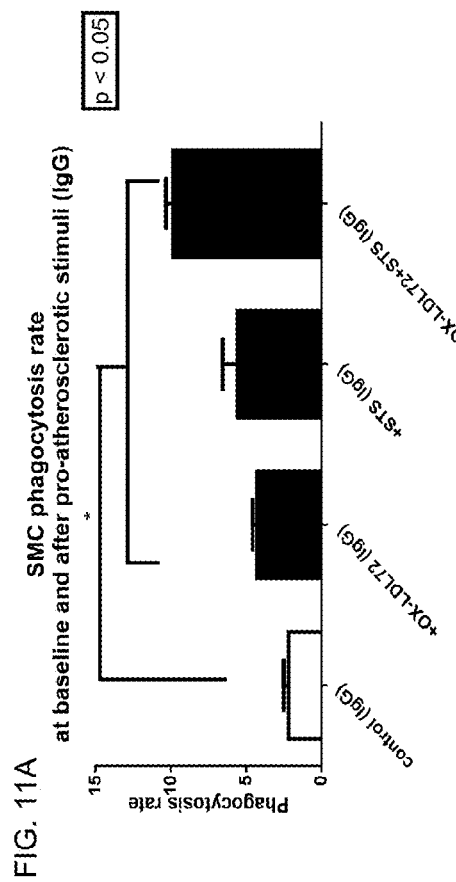
Figure 11C:
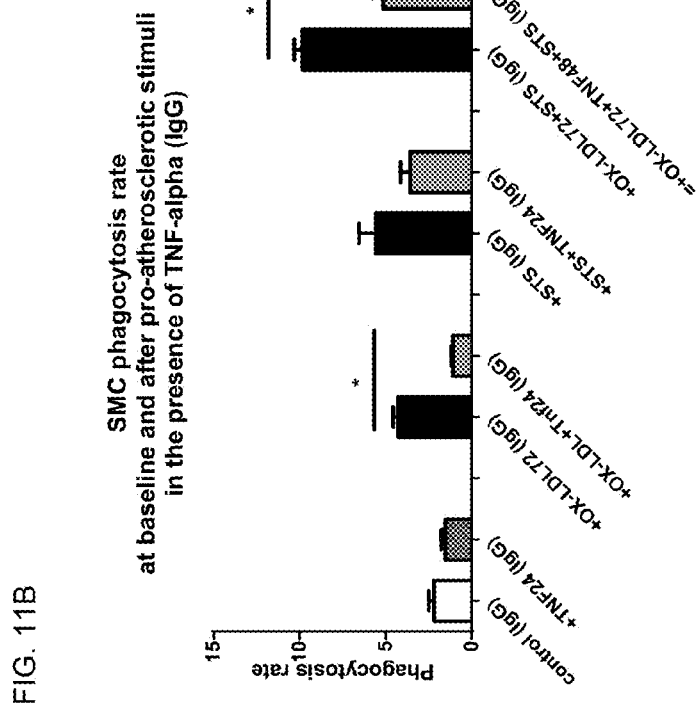
Figure 12:
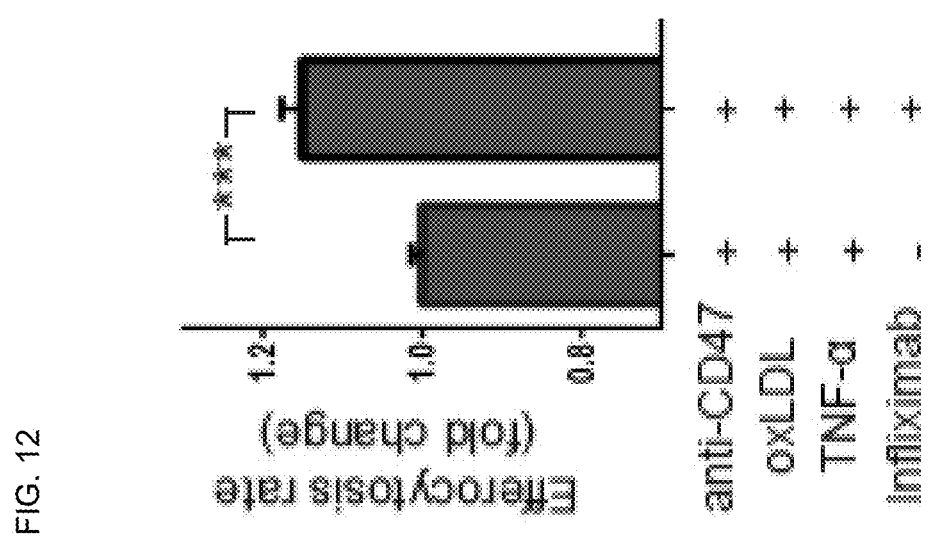
FIG. 12. In vitro data showing that anti-CD47 therapy can synergize with anti-TNF-alpha therapy to promote efferocytosis/phagocytosis. Concomitant inhibition of CD47 and TNFα using anti-CD47 antibody and infliximab, respectively, produces synergistic benefit in the clearance of diseased vascular cells.
Figure 14:
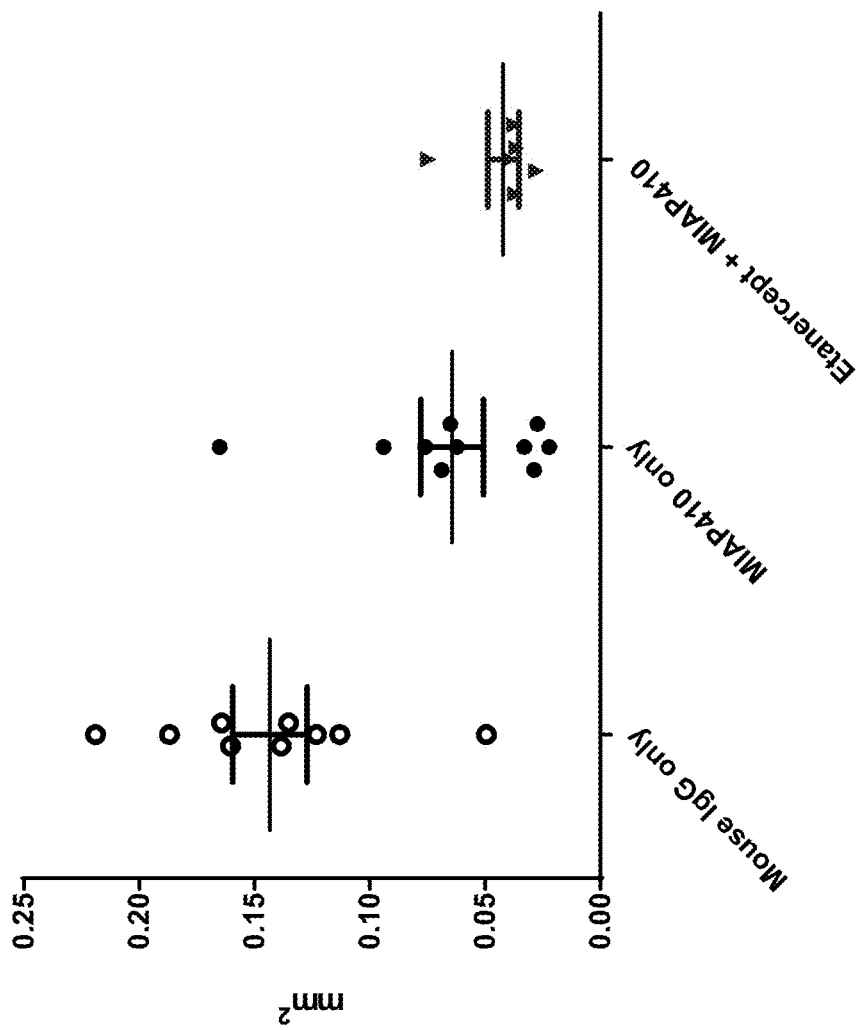
FIG. 14. In vivo data showing that combination therapy (anti-CD47 Ab plus the TNF-$\alpha$ inhibitor Etanercept) reduces atherosclerosis to a greater extent that anti-CD47 Ab (MIAP410) alone. Data presented as Oil Red O positive atherosclerotic area in the aortic sinus of mice.

In vitro phagocytosis assays demonstrate that TNF-alpha impairs the phagocytosis of vascular cells at baseline and under a number of disease conditions including exposure to pro-atherosclerotic lipids and other apoptosis-inducing stimuli (FIG. 11). Our data confirm that anti-CD47 Ab therapy is particularly efficacious in the presence of TNF-alpha and identify dual inhibition of CD47 and TNF-alpha (and its related signaling members) as a target for the prevention and treatment of cardiovascular disease.

Methods:

Murine atherosclerosis studies. Animals used in this study included male $Cdkn2b^{+/+}, ApoE^{-/-}$ (n=27, Jackson Laboratory) and $Cdkn2b^{-/-}, ApoE^{-/-}$ (n=27) mice on a C57BL/6 background, which were bred by our laboratory as previously described. At 4 weeks of age, the animals were weaned and initiated on a high fat Western diet (21% anhydrous milk fat, 19% casein and 0.15% cholesterol, Dyets no. 101511) for the ensuing weeks. Animals were observed daily, and in the case of premature sudden death, necropsy was performed to determine the cause of death. Lipid analysis was performed in mice after an overnight fast, as previously described. In brief, total plasma cholesterol (CHOD-PAP; Roche Diagnostics), HDL (HDL-C-plus 2nd generation; Roche Diagnostics), and LDL concentrations (GPO-PAP; Roche Diagnostics) were measured using enzymatic kits on an automated analyzer (Roche) according to the manufacturer's instructions. Fasting glucose was measured in venous blood from a tail prick using a Freestyle Glucometer and glucose strips (Abbott). At 16 weeks of age, the mice were euthanized and the aortas were isolated and processed for analysis. A subset of ten mice were implanted with subcutaneous osmotic minipumps (Alzet, Model 2004) after only four weeks of high-fat diet, to deliver 1.4 mg/kg/day of Angiotensin II for 72 hours prior to sacrifice to enhance vascular injury in early atherosclerotic lesions. All studies were approved by the Stanford University Administrative Panel on Laboratory Animal Care and conform to the Guide for the Care and Use of Laboratory Animals published by the US National Institutes of Health.

Aortic and brachiocephalic tissue preparation, immunohistochemistry and atherosclerotic lesion quantification. Aortic atherosclerosis lesion area was determined as described previously. Briefly, the arterial tree was perfused with PBS (pH 7.3) and then perfusion fixed with phosphate-buffered paraformaldehyde (3%, pH 7.3). The heart and the full-length of the aorta-to-iliac bifurcation was exposed and dissected carefully from any surrounding tissues. Aortas were then opened along the ventral midline and dissected free of the animal and pinned out flat, intimal side up, onto black wax. Aortic images were captured with a digital camera mounted on a Nikon stereomicroscope and analyzed using Adobe Photoshop CS5 software. The percentage of lesion area was calculated as total lesion area divided by total surface area. The atherosclerotic lesions in aortic valve area and proximal brachiocephalic artery were analyzed as described previously. The samples were perfused with PBS, fixed with paraformaldehyde (4%), embedded in OCT, and sectioned at 7-µM thickness. Three sections at 100-µM intervals were collected from each mouse and stained with Oil Red O (Sigma-Aldrich, O0625), Masson Trichrome (Sigma Aldrich, St. Louis, Mo., USA), Picrosiruis Red (Polysciences, #24901), haematoxylin and eosin (H&E), smooth muscle α-actin (SMA, Abcam, ab5694, 1:300), Mac-3 (BD Sciences BD 550292, 1:75), CD-3 (Abcam, ab5690, 1:150), and Calreticulin (Abcam, ab2907, 1:300). Biotinylated secondary antibodies followed by avidin-biotin-alkaline phosphatase substrate were used as previously described.

In vivo apoptosis was assessed by staining for TUNEL positivity with the Cell Death Detection Kit (Roche), per protocol. Cellular proliferation was measured by staining with PCNA (Abcam, ab2426, 1:500). The cellularity of the vessel was measured by manually counting nuclei of sections stained with DAPI. Negative controls were performed with the omission of the primary antibody. The lesion areas were measured and quantified using Adobe Photoshop. Features of atherosclerotic plaque vulnerability were assessed as previously described. Briefly, the size of the necrotic core was measured by calculating the percentage of the lesion which was acellular on H&E staining. The cap thickness was measured by placing a 12 point compass in the center of the blood vessel and averaging the thickness of the cap at each point as it crossed the lesion. SMC cap coverage was measured by calculating the percentage of the fibrous cap surface which stained positive for SMA-actin. Other standard features were assessed as described. Samples harvested from several tissue beds were also snap frozen in liquid nitrogen for subsequent gene expression analysis, as described below. Electron microscopy was performed in the Cell Sciences Imaging Facility by the Stanford Electron Microscopy Core on a Jeol TEM1230.

Human atherosclerotic plaque harvest and gene coexpression network analysis. Details of sample collection, RNA isolation, and microarray hybridization have been previously described. In brief, epicardial coronary arteries were harvested by dissection from explanted hearts of 22 patient donors for orthotopic heart transplant. Arterial segments were identified as containing atherosclerotic lesions (n=38) or not (n=13) by microscopic inspection. RNA was isolated from each sample and hybridized to a custom dual-dye gene expression microarray (Agilent; Palo Alto, Calif.) representing 20,226 transcripts identified via sequencing clones from stimulated vascular cells, literature review for genes important to cardiovascular function, and combination with a commercial clone set (Incyte). Arrays were scanned using Agilent's G2565AA Microarray Scanner System and Agilent feature extraction software was used to generate log 2 ratios and P values for features on the array. Prior to gene coexpression network analysis, probe set identifiers were mapped to the current NCBI refseq gene build (hg19) and median values were taken for probes matching the same transcript ID. The general framework for weighted gene coexpression network analysis is described.

Pair-wise Pearson correlation between gene expression values was calculated for every gene in the dataset for a) samples with atherosclerotic lesions, b) samples without atherosclerotic lesions, c) all samples. A soft thresholding parameter 13 was chosen to satisfy scale-free topology criterion based on R2 maximization for a linear fit with slope −1 to log(k) vs. log(n(k)), effectively "noising down" weak correlations. The topological overlap between genes was calculated according to the method described by Yip and Horvath, generating a network adjacency based on shared network neighbors for all gene pairs. We next used average linkage hierarchical clustering and the dynamic tree cut algorithm, which iteratively searches for stable clusters, to partition the topological overlap network into modules. Singular value decomposition was used to identify the module "eigengene" (first principle component) representing the maximum variance in modular gene expression, and the intra-modular and global connectivity for each gene was generated by summing edge weights within modules and within the global network, respectively.

For targeted analysis of the topological relationship between CDKN2B and 28 annotated genes involved in efferocytosis (CALR, MFGE8, CX3CL1, ABCA6, ICAM3, GAS6, APOH, PROS1, C1QB, ANXA1, CD47, LRP1, MBL2, SIRPA, NR1H3, PPARG, LRPAP1, TGFB1, BAI1, TIMD4, CD14, MERTK, CD36, ELMO1, DOCK1, AKT1, PANX1, GULP1), average linkage hierarchical clustering was performed on the reduced topological overlap matrix representing all pair-wise links between these set members and CDKN2B. Module assignment and eigengene calculation was performed as described above. Differential expression analysis according to presence or absence of atherosclerotic lesion was performed by Wilcoxon rank sum test between module eigengene expression values. A p value less than 0.05 was considered statistically significant. Network visualization was performed using Cytoscape 2.8.3 (San Diego, Calif.) to the topological overlap matrix.

Cell culture methods. Human coronary artery SMC (HCASMC, Lonza, Walkersville, Md., passage #3-6) were propagated in SmGM-2 growth media (Lonza) containing 5% FBS. Human THP-1 monocytic cells, human embryonic kidney (HEK-293) and RAW 264.7 macrophages (ATCC) were grown in DMEM-growth media containing 10% FBS. Primary vascular smooth muscle cells were harvested from the aortas of $Cdkn2b^{+/+}$ and $Cdkn2b^{-/-}$ mice, as previously described. Primary activated macrophages were harvested from mice 72 hrs after intraperitoneal injection of 2 ml of 4% thioglycollate, as previously described. To induce growth arrest and the expression of differentiation genes, SMC were serum starved in basal media (SmBM) for 72 hours, according to conventional protocols.

To induce differentiation of THP-1 monocytes into adherent macrophages, cells were treated with 100 nM PMA for 72 hours, as previously described. For knockdown experiments, SMC were transfected with 300 nM of anti-CDKN2B (siCDKN2B) or high-GC negative control (si-Cont) siRNA (Ambion, Silencer Select, catalog #4390825 and 4390843, respectively) using the high-efficiency Amaxa Nucleofector system (Lonza, protocol U-025). Successful transfection (>85% of all cells) was confirmed by visual fluorescent microscopic analysis and fluorescence activated cell sorting (FACS) flow cytometry for the fluorescently-labeled positive control, pmax GFP (Amaxa). Plates were harvested at 80% confluence for RNA and protein analysis or used for subsequent in vitro analysis. Reproducible knockdown of CDKN2B was confirmed in SMC by quantitative rt-PCR which displayed selective silencing of this gene on the order of ~85%. No off target knockdown was observed for any of the other nearby genes, including CDKN2A, ARF or ANRIL. Apoptosis was induced by treating HCASMC with 1 μM staurosporine (Sigma, S5921) in serum free media for 6 hours prior to analysis or harvest and use in co-culture experiments.

mRNA isolation and quantitative reverse-transcription. PCR RNA was isolated from cell lysates using the miRNeasy Mini Kit (Qiagen, Valencia, Calif.) according to the manufacturers protocol. RNA was isolated from the murine organ samples using the Trizol method (Invitrogen). RNA was quantified with the Nanodrop machine (Agilent Technologies, Santa Clara, Calif.) For quantitation of gene transcription, cDNA was generated with M-MuLV reverse transcriptase, and then amplified on the ABI PRISM 7900HT with commercially available TaqMan primers (Applied Biosystems, Foster City, Calif.) and normalized to 18S internal controls, as previously described. A list of the primers and probes used in these studies is provided in below.

Primer Species: Human APOH Hs00979406_m1, C1QC Hs00757779_m1, ANRIL Hs01390879_m1, ARF Hs99999189_m1, CDKN2A Hs00923894_m1, CDKN2B Hs00793225_m1, CD47 Hs00179953_m1, CALR Hs00189032_m1, GAS6 Hs01090305_m1, ICAM3 Hs00233674_m1, MFGE8 Hs00170712_m1, MTAP Hs00559618_m1.

Species: Mouse Calreticulin Mm00482936_m1, Cdkn2a Mm00494449_m1, Arf Mm01257348_m1, Cdkn2b Mm00483241_m1, Abca1 Mm00442646_m1.

In vitro assays and promoter analysis, In silico bioinformatics. Transcription factor binding site (TFBS) prediction was determined using the following online bioinformatics tools: TRANSFAC (BIOBASE), TFSearch, PROMO, and MatInspector.

Radioactive electrophoretic gel mobility shift assays. Double stranded oligonucleotides for the top predicted E2F4 binding sites (−150 to −134) within the CALR promoter were generated by annealing the following single stranded oligos: F:5' TGGCAGGGGCGGGCCCAAGGGCTG 3' and R:5' CAGCCCTTGGGCCCGCCCCTGCCA 3'. -ATP (Perkin Elmer) using T4 polynucleotide kinase (NEB) for 30 minutes at room temperature and then purified through Sephadex G-50 Quick Spin columns (Roche). After measuring radioactivity, reactions were assembled with 1×EMSA binding buffer, 1 μg poly-dIdC, 10 μg nuclear extract harvested from HCASMC, 100× unlabeled probe (for competitions), -ATP labeled probe, and incubated at room temperature for 30 min prior to protein separation on a 4% TBE gel. Gels were dried on Whatman paper using a heated vacuum drier and proteins were detected on radiographic film.

Chromatin immunoprecipitation assays Chromatin immunoprecipitation (ChIP) was performed according to the Millipore EZ-ChIP protocol with slight modifications. HCASMC were cultured in normal growth media until approximately 75% confluent, and then cultured in the absence of serum and supplements for 24 hours. Cells were fixed in 1% formaldehyde for 10 minutes to cross-link chromatin, followed by quenching with glycine for 5 minutes at room temperature. $2\times10^7$ cells per condition were collected, and nuclear lysates were prepared as described previously(70). Cross-linked chromatin nuclear extracts were sheared into approximately 500 bp fragments using a Bioruptor (Diagenode) for 3 cycles of 3 minutes (30 s ON, 30 s OFF). Sheared chromatin was clarified via centrifugation at 4 C for 15 minutes. $1\times10^6$ nuclei per condition was precleared with 20 μg anti-rabbit IgG pre-immune serum (Sigma) and 40 μl Protein G Dynabeads (Invitrogen) for 1 hour on a rotating platform, followed by incubation with 2 μg Rabbit IgG or anti-E2F4 antibody (C-20 SC866 Santa Cruz) overnight.

Immunoprecipitated chromatin samples were then incubated with 60 μl Protein G Dynabeads for 2 hours at 4 C on a rotating platform to capture the protein-DNA complexes. Complexes were washed in Low salt, High salt, LiCl, and TE buffers and then eluted with a buffer containing 100 nM NaHCO3 and 1% SDS. Protein-DNA crosslinks were reversed and samples were treated with RNase A and Proteinase K and free DNA was purified using Qiagen PCR purification kits. Total enrichment was measured using primers designed based on the sequence of the top E2F4 binding site within the Calreticulin promoter (F (−199 to −181) :5' AGGTCCAATGGAAAAAGAC 3' and R (+84 to +65) :5' CAGAAACTGCTCCTTGAAGT 3'), or a known E2F4 regulatory region (FGFr1 as a positive control (Devel Dynamics 2005 119), or a Negative Control region using the following primers (F:5' CCGGAAGCACTTCTCCTAGA 3' and R:5' AAGAGAGAGCGGAAGTGACG 3').

Semiquantitative PCR was used to verify ChIP products via gel electrophoresis. Quantitative real-time PCR (ViiA 7, Life Technologies) was performed using SYBR Green (Applied Biosystems) assays and fold enrichment was calculated by measuring the delta Ct-delta Ct IgG. Melting curve analysis was also performed for each ChIP primer. Data are representative of at least four independent HCASMC samples with qPCR assays performed in triplicate. Data is presented as the percentage of Input DNA and as fold enrichment of chromatin precipitated with the E2F4 Ab relative to the control IgG.

Luciferase promoter reporter assays. Calreticulin LightSwitch Promoter Reporter GoClones (RenSP, S721464), Empty vectors (S790005) and Cypridina TK Control constructs (pTK-Cluc, SN0322S) were obtained from SwitchGear Genomics (Menlo Park, Calif.) and transfected into HEK cells using Lipofectamine 2000 (Invitrogen). For knockdown assays, 5 pmol of anti-CDKN2B or control siRNA were co-transfected. For overexpression, CDKN2B (sc319536) and Rb expression plasmid (sc119971) and empty vector (pCMV6) were obtained from Origene and 100 ng of plasmid were co-transfected. Dual luciferase activity was measured with the LightSwitch Dual Assay System after 48 hours using a SpectraMax L luminometer (Molecular Devices), according to the manufacturer's instructions. In some experiments, media was changed to serum-free media after 24 hours of transfection. Studies were performed at baseline, and after the cells had been exposed to escalating doses of recombinant human TGFβ-1 (from Sigma, 0.5-10 ng/mL) for the final 16 hours prior to analysis. Relative luciferase activity (Renilla/Cypridina luciferase ratio) is expressed as the percentage change relative to the basal values obtained from control-transfected cells not exposed to TGF-β treatment.

Efferocytosis resistance and capacity assays. Primary aortic smooth muscle cells generated from $Cdkn2b^{-/-}$ and $Cdkn2b^{+/+}$ mice were labeled with 20 μM orange CMTMR CellTracker fluorescent probes (Life Technologies, C2927) for one hour, then cultured overnight in serum free media. Simultaneously, primary intraperitoneal $Cdkn2b^{+/+}$ macrophages were labeled with 20 μM of green CMFDA CellTracker probe (Life Technologies, C7025) for one hour, then cultured overnight in standard media with serum supplementation. In the morning, the SMCs were induced to undergo apoptosis for 4 hours, then were harvested and manually counted. $1\times10^5$ apoptotic cells were then added to the cultured macrophages and were allowed to co-culture for an additional 1.5 hrs. At that point, all adherent cells were trypsinized and FACS sorted (BD FACSCaliber, 530 nm [FL1] and >575 nm [FL4]), as in previously published protocols. Cells which were dual-positive for green (phagocyte) and orange (SMC) were assumed to represent phagocytosed cells.

The efferocytosis rate was then defined as the percentage of dual positive cells (phagocytosed AB) to orange-positive/green-negative cells (un-eaten AB). Comparison was made between the rates of clearance for $Cdkn2b^{-/-}$ and $Cdkn2b^{+/+}$ AB. This experiment was performed as above with the following permutations: primary murine aortic SMC vs. primary murine intraperitoneal thioglycollate stimulated macrophages; primary murine aortic SMC vs. murine unstimulated RAW macrophages; transfected HCASMC vs. human PMA-stimulated THP-1 cells.

Finally, the effect of CDKN2B on the 'efferocytic capacity' (vs 'efferocytic resistance') was assessed by performing these experiments with CDKN2B deficient and control transfected phagocytes exposed to untransfected AB. In these experiments, the phagocytic capacity was defined as the percentage of dual positive cells (phagocytes which had eaten an AB) to orange-negative/green-positive cells (phagocytes that had not eaten an AB). All assays were repeated on three occasions with at least three replicates per experiment. Analysis was performed with FloJo 7.6.3.

Efferocytosis competition assays. Confirmation of the preceding studies was performed by plating equal numbers of green CellTracker labeled apoptotic siCDKN2B HCASMC and orange CellTracker labeled apoptotic siCont HCASMC onto unlabeled untransfected non-apoptotic HCASMC in 12-well cell culture plates. All three cell types were co-cultured for an additional 2 hours, and then the non-adherent, non-phagocytosed cells were washed off. The remaining cells were fixed and stained with DAPI and analyzed under an inverted fluorescent microscope. 8 random hpf/well were manually counted by a blinded investigator for efferocytosed cells and the ratio of phagocytosed CDKN2B-deficient AB to control-transfected AB was recorded.

Phagocyte-Apoptotic Body co-culture assays Cholesterol efflux culture assays Cholesterol efflux assays were performed as described previously, with modification. RAW macrophages were plated on 12-well plates in DMEM containing 10% FBS and labeled with [3H]cholesterol (0.5 μCi/well) for 48 hours. After washing with PBS, the cells were co-cultured with apoptotic $Cdkn2b^{-/-}$ and $Cdkn2b^{+/+}$ aortic smooth muscle cells for 1.5 hours, then incubated in serum free DMEM overnight. The cells were washed and incubated in 350 μl of serum free media containing 10 μg/ml Apolipoprotein A-1 (Sigma) as an acceptor for 4 hours. The media was collected and centrifuged, and the amount of radioactivity was determined by scintillation counter. Cholesterol efflux was expressed as the percentage of counts in the media versus total [$^3$H] cholesterol counts (media plus cell). Baseline efflux (without apoA-1) was subtracted.

Foam cell formation assays. RAW macrophages were seeded on 96-well plates and cultured overnight. In some experiments, macrophages were treated with 100 ng/ml of Lipopolysaccharide from *Escherichia coli* O111:B4 (LPS, Sigma). Macrophages were co-cultured with apoptotic $Cdkn2b^{-/-}$ and $Cdkn2b^{+/+}$ aortic smooth muscle cells and 100 μg/ml oxidized LDL (Biomedical Technologies Inc.) for 24 hrs. The cells were fixed in 4% paraformaldehyde for 20 min, washed with PBS, and stained with 0.5% oil red O for 5 min. After rinsing in 60% isopropanol and washing, 8 random images/well were taken with an inverted microscope at 20× magnification. Oil red O positive area was analyzed with Adobe Photoshop CS5 software.

Macrophage-specific cytokine expression assays LPS-stimulated (1 μg/mL) RAW macrophages were co-cultured with either siCDKN2B or siCont apoptotic HCASMC in serum free media. Unattached HCASMC was removed by washing with PBS after 1.5 hours, then the cells were cultured in serum free DMEM. After 24 hours of incubation, the supernatant was collected and the level of secreted IL-10 and TNF-α was assessed with ELISAs (R&D Systems) developed specifically for cytokines of murine origin.

Statistical analysis Data are presented as mean±SEM. Data were subjected to the Kolmogorov-Smirnov test to determine distribution. Groups were compared using the Mann-Whitney U test for non-parametric data or the Students t-test for parametric data. When comparing multiple groups, data were analyzed by analysis of variance with Bonferroni's post test. For multiple testing of parametric data, a value of $P<0.05$ was considered statistically significant. Experiments were replicated at least in quadruplicate and all analyses were performed in a blinded fashion by two separate investigators, unless otherwise specified. Statistical analysis was performed with GraphPad Prism 5.

What is claimed is:

1. A method of reducing atherosclerotic plaque in a human subject, the method comprising:
   genotyping the subject for the presence of at least one 9p21 risk allele, where an individual determined to have a 9p21 risk allele for atherosclerosis is treated by administering to the subject an effective dose of an anti-CD47 antibody and an anti-TNFα antibody, thereby inhibiting atherosclerotic plaque.

2. The method of claim 1, wherein the anti-CD47 antibody reduces the binding of CD47 on an apoptotic cell to SIRPα on a phagocytic cell.

3. The method of claim 1, wherein the 9p21 risk allele is genotyped by determination of the presence of a single nucleotide polymorphism (SNP) variant selected from: rs3217992, rs4977574, rs3217989, rs1333040, rs10116277, rs7044859, rs1292136, rs7865618, rs9632884, rs10757272, rs2891168, rs6475606, rs1333048, and rs1333045.

4. The method of claim 1, wherein the anti-TNFα agent is selected from: Etanercept, Infliximab, and SPD 304.

5. A method of reducing atherosclerotic plaque in a human subject, the method comprising:
   selecting a human subject known to be comprising at least one 9p21 risk allele, where an individual with a 9p21 risk allele for atherosclerosis is treated by administering to the subject an effective dose of an anti-CD47 antibody and an anti-TNFα antibody, thereby inhibiting atherosclerotic plaque.

6. The method of claim 5, wherein the human subject is known to comprise a single nucleotide polymorphism (SNP) variant selected from: rs3217992, rs4977574, rs3217989, rs1333040, rs10116277, rs7044859, rs1292136, rs7865618, rs9632884, rs10757272, rs2891168, rs6475606, rs1333048, and rs1333045.

* * * * *